(12) United States Patent
Bornhop et al.

(10) Patent No.: US 9,562,853 B2
(45) Date of Patent: Feb. 7, 2017

(54) NONAQUEOUS BACKSCATTERING INTERFEROMETRIC METHODS

(75) Inventors: Darryl J. Bornhop, Nashville, TN (US); Robert A. Flowers, Nazareth, PA (US); Esther Pesciotta Miller, Yardley, PA (US)

(73) Assignee: Vanderbilt University, Nashville, TN (US)

( * ) Notice: Subject to any disclaimer, the term of this patent is extended or adjusted under 35 U.S.C. 154(b) by 144 days.

(21) Appl. No.: 13/402,104

(22) Filed: Feb. 22, 2012

(65) Prior Publication Data

US 2013/0021608 A1 Jan. 24, 2013

Related U.S. Application Data

(60) Provisional application No. 61/445,352, filed on Feb. 22, 2011.

(51) Int. Cl.
*G01N 21/45* (2006.01)
*G01N 21/47* (2006.01)

(52) U.S. Cl.
CPC ....... *G01N 21/45* (2013.01); *G01N 2021/4709* (2013.01)

(58) Field of Classification Search
CPC ............ G01N 21/45; G01N 2021/4709; G01N 21/4133
USPC .................................................. 356/481, 517
See application file for complete search history.

(56) References Cited

U.S. PATENT DOCUMENTS

| | | | |
|---|---|---|---|
| 3,567,113 A | 3/1971 | Stansell et al. |
| 3,687,808 A | 8/1972 | Clercq et al. |
| 4,093,759 A | 6/1978 | Otsuki et al. |
| 4,265,554 A | 5/1981 | Clancy et al. |
| 4,268,554 A | 5/1981 | Gras |
| 4,443,106 A | 4/1984 | Yasuda et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,660,974 A | 4/1987 | Machler et al. |
| 4,667,025 A | 5/1987 | Miyoshi et al. |
| 4,683,195 A | 7/1987 | Mullis et al. |
| 4,683,202 A | 7/1987 | Mullis |
| 4,699,951 A | 10/1987 | Allenson et al. |
| 4,762,779 A | 8/1988 | Snitman |
| 4,789,737 A | 12/1988 | Miyoshi et al. |

(Continued)

FOREIGN PATENT DOCUMENTS

| | | |
|---|---|---|
| CA | 2584824 A1 | 5/2006 |
| CH | 00959154.6 | 8/2000 |

(Continued)

OTHER PUBLICATIONS

U.S. Appl. No. 13/401,303, filed Feb. 21, 2012, Darryl J. Bornhop.

(Continued)

*Primary Examiner* — Hwa Lee
(74) *Attorney, Agent, or Firm* — Ballard Spahr LLP

(57) ABSTRACT

Disclosed are improved optical detection methods comprising multiplexed interferometric detection systems and methods for determining a characteristic property of a nonaqueous sample, together with various applications of the disclosed techniques.

20 Claims, 5 Drawing Sheets

(56) References Cited

U.S. PATENT DOCUMENTS

| | | |
|---|---|---|
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,876,335 A | 10/1989 | Yamane et al. |
| 4,895,431 A | 1/1990 | Tsujiuchi et al. |
| 4,904,582 A | 2/1990 | Tullis |
| 4,908,112 A | 3/1990 | Pace |
| 4,948,882 A | 8/1990 | Ruth |
| 4,950,074 A | 8/1990 | Fabricius et al. |
| 4,958,013 A | 9/1990 | Letsinger |
| 4,976,154 A | 12/1990 | Schneider et al. |
| 4,981,957 A | 1/1991 | Lebleu et al. |
| 4,990,925 A | 2/1991 | Edelsohn et al. |
| 5,023,243 A | 6/1991 | Tullis |
| 5,034,506 A | 7/1991 | Summerton et al. |
| 5,073,024 A | 12/1991 | Valette et al. |
| 5,082,830 A | 1/1992 | Brakel et al. |
| 5,108,179 A | 4/1992 | Myers |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,120,131 A | 6/1992 | Lukosz |
| 5,125,740 A | 6/1992 | Sato et al. |
| 5,130,302 A | 7/1992 | Spielvogel et al. |
| 5,134,066 A | 7/1992 | Rogers et al. |
| 5,138,045 A | 8/1992 | Cook et al. |
| 5,165,005 A | 11/1992 | Klainer et al. |
| 5,166,315 A | 11/1992 | Summerton et al. |
| 5,173,747 A | 12/1992 | Boiarski et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,215,883 A | 6/1993 | Chu |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,268,305 A | 12/1993 | Ribi et al. |
| 5,272,250 A | 12/1993 | Spielvogel et al. |
| 5,273,633 A | 12/1993 | Wang |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,304,487 A | 4/1994 | Wilding et al. |
| 5,305,071 A | 4/1994 | Wyatt |
| 5,309,330 A | 5/1994 | Pillers et al. |
| 5,317,098 A | 5/1994 | Shizuya et al. |
| 5,319,080 A | 6/1994 | Leumann |
| 5,321,131 A | 6/1994 | Agrawal et al. |
| 5,325,170 A | 6/1994 | Bornhop |
| 5,350,697 A | 9/1994 | Swope et al. |
| 5,351,678 A | 10/1994 | Clayton et al. |
| 5,359,044 A | 10/1994 | Cook et al. |
| 5,367,066 A | 11/1994 | Urdea et al. |
| 5,371,241 A | 12/1994 | Brush |
| 5,377,008 A | 12/1994 | Ridgway et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,426,505 A | 6/1995 | Geiser et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,456,245 A | 10/1995 | Bornhop et al. |
| 5,456,885 A | 10/1995 | Coleman et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,479,257 A | 12/1995 | Hashimoto |
| 5,484,908 A | 1/1996 | Froehler et al. |
| 5,485,277 A | 1/1996 | Foster |
| 5,485,312 A | 1/1996 | Horner et al. |
| 5,486,603 A | 1/1996 | Buhr |
| 5,489,677 A | 2/1996 | Sanghvi et al. |
| 5,502,177 A | 3/1996 | Matteucci et al. |
| 5,502,561 A | 3/1996 | Hutchins et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,852 A | 9/1996 | Nakamura et al. |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,578,832 A | 11/1996 | Trulson et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,593,839 A | 1/1997 | Hubbell et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,695 A | 2/1997 | Pease et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,613,013 A | 3/1997 | Schuette |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,631,734 A | 5/1997 | Stern et al. |

(56) References Cited

U.S. PATENT DOCUMENTS

| | | |
|---|---|---|
| 5,633,312 A | 5/1997 | Kabeta et al. |
| 5,633,360 A | 5/1997 | Bischofberger et al. |
| 5,633,708 A | 5/1997 | Svendsen |
| 5,636,017 A | 6/1997 | Bruno et al. |
| 5,639,873 A | 6/1997 | Barascut et al. |
| 5,646,265 A | 7/1997 | McGee |
| 5,658,873 A | 8/1997 | Bertsch-Frank et al. |
| 5,659,318 A | 8/1997 | Madsen et al. |
| 5,663,312 A | 9/1997 | Chaturvedula |
| 5,663,790 A | 9/1997 | Ekstrom et al. |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,694,210 A | 12/1997 | Newell et al. |
| 5,698,518 A | 12/1997 | Carson et al. |
| 5,700,920 A | 12/1997 | Altmann et al. |
| 5,712,321 A | 1/1998 | Cantor et al. |
| 5,714,331 A | 2/1998 | Buchardt et al. |
| 5,719,262 A | 2/1998 | Buchardt et al. |
| 5,740,291 A | 4/1998 | De Lasa et al. |
| 5,770,029 A | 6/1998 | Nelson et al. |
| 5,781,304 A | 7/1998 | Kotidis et al. |
| 5,804,453 A | 9/1998 | Chen |
| 5,815,258 A | 9/1998 | Nakanishi |
| 5,817,462 A | 10/1998 | Garini et al. |
| 5,824,204 A | 10/1998 | Jerman |
| 5,841,914 A | 11/1998 | Shieh et al. |
| 5,846,708 A | 12/1998 | Hollis et al. |
| 5,852,495 A | 12/1998 | Parce |
| 5,867,266 A | 2/1999 | Craighead |
| 5,915,034 A | 6/1999 | Nakajima et al. |
| 5,922,594 A | 7/1999 | Lofås |
| 5,928,627 A | 7/1999 | Kiefer et al. |
| 5,932,474 A | 8/1999 | Tsien et al. |
| 5,953,439 A | 9/1999 | Ishihara et al. |
| 5,976,336 A | 11/1999 | Dubrow et al. |
| 5,995,645 A | 11/1999 | Soenksen et al. |
| 6,008,378 A | 12/1999 | Tsien et al. |
| 6,054,271 A | 4/2000 | Tsien et al. |
| 6,108,458 A | 8/2000 | Hart |
| 6,123,798 A | 9/2000 | Gandhi et al. |
| 6,130,439 A * | 10/2000 | Le Menn ............... 250/573 |
| 6,167,910 B1 | 1/2001 | Chow |
| 6,198,532 B1 | 3/2001 | Cabib et al. |
| 6,251,343 B1 | 6/2001 | Dubrow et al. |
| 6,321,791 B1 | 11/2001 | Chow |
| 6,322,683 B1 | 11/2001 | Wolk et al. |
| 6,381,025 B1 | 4/2002 | Bornhop et al. |
| 6,381,925 B2 | 5/2002 | Rejcek et al. |
| 6,451,569 B1 | 9/2002 | Tsien et al. |
| 6,480,282 B1 | 11/2002 | Chinowsky et al. |
| 6,493,090 B1 | 12/2002 | Lading et al. |
| 6,529,279 B2 | 3/2003 | de Groot et al. |
| 6,532,061 B2 | 3/2003 | Ortyn et al. |
| 6,533,914 B1 | 3/2003 | Liu |
| 6,559,947 B1 | 5/2003 | Turner |
| 6,576,430 B1 | 6/2003 | Hsieh et al. |
| 6,660,517 B1 | 12/2003 | Wilding et al. |
| 6,741,361 B2 | 5/2004 | Marron |
| 6,744,950 B2 | 6/2004 | Aleksoff |
| 6,760,103 B2 | 7/2004 | Shakespeare et al. |
| 6,798,509 B2 | 9/2004 | Sonehara et al. |
| 6,809,828 B2 | 10/2004 | Bornhop et al. |
| 6,962,690 B2 | 11/2005 | Kiefer et al. |
| 6,980,299 B1 | 12/2005 | de Boer |
| 7,045,171 B2 | 5/2006 | Bookbinder et al. |
| 7,130,060 B2 | 10/2006 | Bornhop et al. |
| 7,172,897 B2 | 2/2007 | Blackburn et al. |
| 7,173,986 B2 | 2/2007 | Wu |
| 7,202,076 B2 | 4/2007 | Cunningham et al. |
| 7,300,803 B2 | 11/2007 | Lin et al. |
| 7,835,013 B2 | 11/2010 | Jones et al. |
| 8,120,777 B2 | 2/2012 | Weinberger et al. |
| 8,134,707 B2 | 3/2012 | Bornhop et al. |
| 8,445,217 B2 | 5/2013 | Bornhop |
| 8,450,118 B2 | 5/2013 | Weinberger et al. |
| 2001/0045358 A1 | 11/2001 | Kopf-Sill et al. |
| 2001/0050821 A1 | 12/2001 | Bickleder et al. |
| 2002/0002353 A1 | 1/2002 | Michal et al. |
| 2002/0022603 A1 | 2/2002 | Lichtenberger |
| 2002/0034580 A1 | 3/2002 | Yang et al. |
| 2002/0057432 A1 | 5/2002 | Ortyn et al. |
| 2002/0094528 A1 | 7/2002 | Salafsky |
| 2002/0128234 A1 | 9/2002 | Hubbell et al. |
| 2002/0135772 A1 | 9/2002 | Bornhop |
| 2003/0082516 A1 | 5/2003 | Straus |
| 2003/0087099 A1 | 5/2003 | Merrill et al. |
| 2003/0099598 A1 | 5/2003 | Kiefer et al. |
| 2003/0129579 A1 | 7/2003 | Bornhop et al. |
| 2003/0148922 A1 | 8/2003 | Knapp et al. |
| 2004/0058058 A1 | 3/2004 | Shchegolikhin et al. |
| 2004/0110276 A1 | 6/2004 | Amontov et al. |
| 2004/0115721 A1 | 6/2004 | Mao et al. |
| 2004/0218184 A1 | 11/2004 | Jorgenson et al. |
| 2004/0241765 A1 | 12/2004 | Zweig |
| 2005/0004348 A1 | 1/2005 | Miyamoto et al. |
| 2005/0014179 A1 | 1/2005 | Karlsson et al. |
| 2005/0019956 A1 | 1/2005 | Martin et al. |
| 2005/0083505 A1 | 4/2005 | Augustyn et al. |
| 2005/0106570 A1 | 5/2005 | Kataoka et al. |
| 2005/0175273 A1 | 8/2005 | Iida et al. |
| 2005/0190372 A1 | 9/2005 | Dogariu |
| 2005/0227374 A1 | 10/2005 | Cunningham |
| 2005/0244863 A1 | 11/2005 | Mir |
| 2005/0264819 A1 | 12/2005 | Arnz et al. |
| 2006/0012777 A1 | 1/2006 | Talbot et al. |
| 2006/0012800 A1* | 1/2006 | Bornhop et al. ............. 356/517 |
| 2006/0039004 A1 | 2/2006 | de Boer et al. |
| 2006/0147379 A1 | 7/2006 | Bornhop et al. |
| 2006/0256343 A1 | 11/2006 | Choma et al. |
| 2006/0263777 A1 | 11/2006 | Tong |
| 2006/0268260 A1 | 11/2006 | Liu et al. |
| 2006/0275179 A1 | 12/2006 | Viovy et al. |
| 2006/0275825 A1 | 12/2006 | Baird et al. |
| 2007/0012777 A1 | 1/2007 | Tsikos et al. |
| 2007/0048747 A1 | 3/2007 | Leslie et al. |
| 2007/0054339 A1 | 3/2007 | Lin et al. |
| 2007/0146888 A1 | 6/2007 | Schmidt et al. |
| 2007/0195321 A1 | 8/2007 | Soussaline et al. |
| 2008/0160187 A1 | 7/2008 | Murata et al. |
| 2008/0182239 A1 | 7/2008 | Mullinax et al. |
| 2008/0186488 A1 | 8/2008 | Kiesel et al. |
| 2008/0194723 A1 | 8/2008 | Hwang et al. |
| 2008/0259313 A1 | 10/2008 | Berndt |
| 2009/0009759 A1 | 1/2009 | Backman et al. |
| 2009/0103091 A1* | 4/2009 | Jones et al. ................. 356/342 |
| 2009/0135421 A1 | 5/2009 | Oldham et al. |
| 2009/0155832 A1 | 6/2009 | Lo et al. |
| 2009/0185190 A1 | 7/2009 | Weinberger et al. |
| 2009/0325199 A1 | 12/2009 | Geddes |
| 2010/0027008 A1 | 2/2010 | Bornhop |
| 2010/0099203 A1 | 4/2010 | Chang et al. |
| 2010/0184056 A1 | 7/2010 | Weinberger et al. |
| 2010/0188665 A1 | 7/2010 | Dotson et al. |
| 2010/0191482 A1 | 7/2010 | Hasson et al. |
| 2011/0109907 A1 | 5/2011 | Meyers et al. |
| 2011/0155927 A1 | 6/2011 | Mitchell et al. |
| 2011/0157692 A1 | 6/2011 | Lin et al. |
| 2012/0015376 A1 | 1/2012 | Bornhop |
| 2012/0019834 A1* | 1/2012 | Bornhop ..................... 356/517 |
| 2012/0176627 A1 | 7/2012 | Weinberger |
| 2012/0199742 A1 | 8/2012 | Wagner et al. |
| 2013/0021608 A1 | 1/2013 | Bornhop et al. |
| 2013/0040306 A1 | 2/2013 | Bornhop et al. |
| 2013/0280715 A1 | 10/2013 | Bornhop et al. |
| 2013/0301055 A1 | 11/2013 | Bornhop et al. |
| 2013/0309661 A1 | 11/2013 | Bornhop |

FOREIGN PATENT DOCUMENTS

| | | |
|---|---|---|
| DE | 00959154.6 | 8/2000 |
| DK | 00959154.6 | 8/2000 |

(56) References Cited

FOREIGN PATENT DOCUMENTS

| EP | 0721016 A2 | 7/1996 |
|---|---|---|
| EP | 0728520 A1 | 8/1996 |
| EP | 0785280 A2 | 7/1997 |
| EP | 0799797 A1 | 10/1997 |
| EP | 00959154.6 | 8/2000 |
| EP | 1210581 A1 | 6/2002 |
| EP | 05821243.2 | 10/2005 |
| EP | 1746385 A1 | 1/2007 |
| EP | 1805498 A2 | 7/2007 |
| EP | 8755681.7 | 5/2008 |
| EP | 10729387 | 1/2010 |
| EP | 2160590 A1 | 3/2010 |
| EP | 2386060 A2 | 11/2011 |
| FR | 2 766 922 A1 | 2/1999 |
| FR | 00959154.6 | 8/2000 |
| GB | 00959154.6 | 8/2000 |
| NL | 00959154.6 | 8/2000 |
| SE | 00959154.6 | 8/2000 |
| WO | WO-95/22058 A1 | 8/1995 |
| WO | WO-97/02357 A1 | 1/1997 |
| WO | WO-97/27317 | 7/1997 |
| WO | WO-97/29212 A1 | 8/1997 |
| WO | PCT/US2000/20783 | 8/2000 |
| WO | WO-01/14858 A1 | 3/2001 |
| WO | WO-02/059579 A1 | 8/2002 |
| WO | WO-2004/023115 A1 | 3/2004 |
| WO | PCT/US2005/38168 | 10/2005 |
| WO | WO-2006/047408 A2 | 5/2006 |
| WO | WO-2007/002178 A2 | 1/2007 |
| WO | PCT/US2008/063879 | 5/2008 |
| WO | PCT/US2008/077145 | 9/2008 |
| WO | WO-2008/144496 A1 | 11/2008 |
| WO | WO-2009/039466 A1 | 3/2009 |
| WO | PCT/US2010/000047 | 1/2010 |
| WO | WO-2010/080710 A2 | 7/2010 |
| WO | WO-2010/129494 A2 | 11/2010 |
| WO | PCT/US2011/039982 | 6/2011 |
| WO | PCT/US2011/056171 | 10/2011 |
| WO | WO-2011/156713 A1 | 12/2011 |
| WO | WO-2012/051429 A1 | 4/2012 |

OTHER PUBLICATIONS

U.S. Appl. No. 60/149,459, filed Aug. 19, 1999, Darryl J. Bornhop.
U.S. Appl. No. 60/263,760, filed Jan. 25, 2001, Darryl J. Bornhop.
U.S. Appl. No. 13/409,557, filed Mar. 1, 2012, Darryl J. Bornhop.
U.S. Appl. No. 61/645,660, filed May 11, 2012, Darryl J. Bornhop.
U.S. Appl. No. 60/620,661, Bornhop et al.
U.S. Appl. No. 60/973,829, Jones et al.
U.S. Appl. No. 60/973,829, Bornhop.
U.S. Appl. No. 60/991,599, Jones et al.
U.S. Appl. No. 61/012,752, Weinberger et al.
U.S. Appl. No. 61/106,552, Bornhop et al.
U.S. Appl. No. 61/144,054, Weinberger et al.
U.S. Appl. No. 61/354,045, Bornhop et al.
U.S. Appl. No. 61/392,890, Bornhop et al.
U.S. Appl. No. 61/445,352, Bornhop et al.
U.S. Appl. No. 61/447,802, Bornhop et al.
Abato P, "An enzymatic method for determining enantiomeric excess," *Journal of the American Chemical Society*, 123: 9206-9207 (2001).
Abbas AK, et al., Cellular and Molecular Immunology (Saunders, Philadelphia, ed. Fifth, 2003).
Adanyi, et al., "Development of immunosensor based on OWLS technique for determining Aflatoxin B1 and Ochratoxin A," Biosens Bioe/ectron 22:797-802 (2007).
Ahlert J, et al., "The calicheamicin gene cluster and its iterative type I enediyne PKS," *Science*, 297: 1173-1176 (2002).
Alunni S, et al., "Mechanisms of inhibition of phenylalanine ammonia-lyase by phenol inhibitors and phenol/glycine synergistic inhibitors," *Archives of Biochemistry and Biophysics*, 412: 170-175 (2003).

Anderson JR, et al., "Fabrication of topologically complex three-dimensional microfluidic systems in PDMS by rapid prototyping," *Analytical Chemistry*, 72: 3158-3164 (2000).
Andersson, et al., "TV sherography: quantitative measurement of shear-magnitude fields by use of digital speckle photography," *Applied Optics*, 39: 2565 (2000).
Anuta, "Digital Registration of Multispectral Video Imagery," Society of Photooptical Instrumentation Engineers Journal, vol. 7:168 (1969).
Arnold F, et al., "Directed Enzyme Evolution," *Methods in Molecular Biology*, 230 (2003).
Arnold FH, "Design by directed evolution," *Accounts of Chemical Research*, 31: 125-131 (1998).
Bachmann BO, et al., "Kinetic mechanism of the β-lactam synthetase of Streptomyces clavuligerus," *Biochemistry*, 39: 11187-11193 (2000).
Bachmann O, et al., "Beta-Lcatam synthetase: A new biosynthetic enzyme," *Proc. Nat. Acad. Sci. USA*, 95: 9082-9086 (1998).
Baksh MM, et al., "Label-free quantification of membrane-ligand interactions using backscattering interferometry," *Nature Biotechnology*, 29: 357-360 (2011).
Baldino F, et al., "High-resolution in situ hybridization histochemistry," *Methods Enzymol*, 168: 761-777 (1989).
Bobbitt DR, et al., "Direct and Indirect Polarimetry for Detection in Micro bore Liquid-Chromatography," *Analytical Chemistry*, 56: 1577-1581 (1984).
Bohren CF, et al., "Absorption and Scattering of Light by Small Particles," New York: Wiley (1983).
Borman S, "Combinatorial chemistry," *Chemical & Engineering News*, 80: 43 (2002).
Bornhop DJ, et al., "Polarimetry in capillary dimensions," *Analytical Chemistry*, 68: 1677-1684 (1996).
Bornhop, "Microvolume index of refraction determinations by interferometric backscatter," Applied Optics, val. 34:3234-3239 (1995).
Bornhop, et al., "Free-Solution, Label-Free Molecular Interactions Studied by Back-Scattering Interferometry," Science, val. 317 No. 5485:1732-1736 (2007).
Bouchara, "Efficient algorithm for computation of the second-order moment of subpixel-edge position," Applied Optics, vol. 43:4550 (2004).
Brawer, et al., "Screening for prostatic carcinoma with prostate specific antigen," J. Ural., 147:841-845 (1992).
Bray P, et al., "Human cDNA clones for four species of G Alpha s signal transduction protein," *Proc Natl Sci USA*, 83: 8893-8897 (1986).
Brenan, et al., "High throughput, nanoliter quantitative PCR," Drug Discovery Today: Tech, 2:247-253 (2005).
Brockhaus et al., "Thermadynamic studies on the interaction of antibodies with β-amyloid peptide," J Phys Chem B, 111:1238-1243 (2007).
Brockman et al., "A Multistep Chemical Modification Procedure to Create DNA Arrays on Gold Surfaces for the Study of Protein-DNA Interactions with Surface Plasmon Resonance Imaging," *J Am Chem Soc*, vol. 121 issue 35:8044-8051 (1999).
Burggraf N, et al., "Holographic Refractive Index Detector for Application in Microchip-based Separation Systems," *Analyst*, 123: 1443-1447 (1998).
Burke et al., "Stopped-flow enzyme assays on a chip using a microfabricated mixer," *Anal Chem*, 75(8):1786-1791 (2003).
Buynak JD, et al., "7-alkylidenecephalosporin esters as inhibitors of human leukocyte elastase," *J. Med. Chem.*, 40: 3423-3433 (1997).
Buynak JD, et al., "Synthesis and Mechanistic Evaluation of 7-Vinylidenecephem Sulfones as P-Lactamase Inhibitors," *J. Am. Chem. Soc.*, 116: 10955-10965 (1994).
Buynak JD, et al., "The Synthesis and β-Lactamase Inhibitory Activity of 6-(Carboxymethylene)Penicillins and 7-(Carboxymethylene) Cephalosporins," *Bioorg. Med. Chem. Lett.*, 5: 1513-1518 (1995).
Campitelli et al., "Shear horizontal surface acoustic wave based immunosensing system," *Int Conf on Solid State Sensors and Actuators*, Jun. 16-19, 1:187-190 (1997).

(56) References Cited

OTHER PUBLICATIONS

Choquette et al., "Wavenumber Standards for Near-infrared Spectrometry," Handbook of Vibrational Spectroscopy, John M. Chalmers and Peter R. Griffiths (Editors), 2002, p. 1-7.
Cohen N, et al., "In vitro enzyme evolution: the screening challenge of isolating the one in a million," *Trends in Biotechnology*, 19: 507-510 (2001).
Collignon et al., "Automated multimodality image registration based on information theory", Information Processing in Medical Imaging (Y. Bizais, C. Barillot and R. Di Paola, eds.), Kluwer Academic Publishers, Dordrecht, pp. 263-274, (1995).
Crooke St, et al., "Pharmacokinetic properties of several novel oligonucleotide analogs in mice," *J Pharmacol Exp Ther*, 277: 923-937 (1996).
DeGrandpre, "Measurement of seawater pCO2 using a renewable-reagent fiber optic sensor with colorimetric detection," *Anal. Chem.*, 65: 331-337 (1993).
Dendane et al., "Surface patterning of (bio)molecules onto the inner wall of fused-silica capillary tubes," *Lab Chip*, 8: 2161 (2008).
Deng Y, et al., "On-column Refractive-index detection Based on Retroreflected Beam Interference for Capillary Electrophoresis," *Applied Optics*, 37(6): 998-1005 (1998).
Ditchburn RW, "Light," Third Ed. Ed. New York: Academic Press (1976).
Dotson SS, et al., "Development of the Ultra Small Volume Polarimeter," Manuscript, Vanderbilt University, 1-11.
Duffy DC, et al., "Rapid Prototyping of Microfluidic Systems in Poly(dimethylsiloxane)," *Analytical Chemistry*, 70: 4974-4984 (1998).
Fan, et al., " Electrochemical interrogation of conformational changes as a reagentless method for the sequence-specific detection of DNA" Proc Natl Acad Sci U S A, 100(16): 9134-9137 (2003).
Finn MG, "Emerging methods for the rapid determination of enantiomeric excess," *Chirality*, 14: 534-540 (2002).
Fintschenko Y, et al., "Silicon Microtechnology and Microstructures in Separation Science," *Journal of Chromotography A*, 819: 3-12 (1998).
Fox SJ, et al., "Assay Innovations Vital to Improving HTS," *Drug Discovery and Development*, 40-43 (2000).
Fricke-Begemann et al., "Speckle interferometry: three-dimensional deformation field measurement with a single interferogram," Applied Optics, vol. 40:5011 (2001).
Gavutis, et al., "Lateral ligand-receptor interaction on membranes probed by simultaneous fluorescence-interference detection," *Biophysics Journal*, 88(6): 4289-4302 (2005).
Gibbs PR, et al., "Imaging polarimetry for high throughput chiral screening," *Biotechnology Progress*, 19: 1329-1334 (2003).
Gloge A, et al., "The behavior of substrate analogues and secondary deuterium isotope effects in the phenylalanine ammonia-lyase reaction," *Archives of Biochemistry and Biophysics*, 359: 1-7 (1998).
Gloge A, et al., "Phenylalanine ammonia-lyase: The use of its broad substrate specificity for mechanistic investigations and biocatalysis—Synthesis of Larylalanines," *Chemistry-a European Journal*, 6: 3386-3390 (2000).
Grant CHE 0848788 awarded by the National Science Foundation.
Grant No. F49620-01-1-0429.
Grant No. R01 EB003537-01A2 awarded by National Institutes of Health.
Greisen, et al., "PCR primers and probes for the 16S rRNA gene of most species of pathogenic bacteria, including bacteria found in cerebrospinal fluid," J Clin Microbiol, 32:335-351 (1994).
Grosse A, et al., "Deep wet etching of fused silica glass for hollow capillary optical leaky waveguides in microfluidic devices," *Journal of Micromechanics and Microengineering*, 11: 257-262 (2001).
Guizar-Sicairos et al., "Efficient subpixel image registration algorithms," Optics Letters, vol. 33:156-158 (2008).
Guo JH, et al., "Measurement of enantiomeric excess by kinetic resolution and mass spectrometry," *Angewandte Chemie-International Edition*, 38: 1755-1758 (1999).

Harrison DJ, et al., "Capillary Electrophoresis and Sample Injection Systems Integrated on a Planar Glass Chip," *Analytical Chemistry*, 64: 1926-1932 (1992).
Harteveld et al., "Detection of Staphylococcal Enterotoxin B employing a piezoelectric crystal immunosensor," *Biosens Bioelectron* 12(7):661-667 (1997).
Hecht E, "Optics," New York: Addison-Wesley Longman (1998).
Heideman, et al., "Remote opto-chemical sensing with extreme sensitivity: design, fabrication and performance of a pigtailed integrated optical phase-modulated Mach-Zehnder interferometer system," *Sensors and Actuators*, B 61: 100-127 (1999).
Heikkinen H, et al., "Interpretation of interference signals in label free integrated interferometric biosensors," *Proceedings of the SPIE*, 6094: 60940P-1 (2006).
Hodgins DS, "Yeast Phenylalanine Ammonia-Lyase—Purification, Properties, and Identification of Catalytically Essential Dehydroalanine," Journal of Biological Chemistry, 246:2977 (1971).
Hofstetter O, et al., "Antibodies as chiral selectors for the determination of enantioenrichment," Enantiomer, 6: 153-158 (2001).
Horton et al., "Interference patterns of a plane-polarized wave from a hollow glass fiber," *J Opt Soc Am*, 63:1204-1210 (1973).
Hubbard et al., "Calmodulin binding by calcineurin," *J Biol Chem* 262(31):15062-15070 (1987).
Hudlicky TM, et al., "Microbial Oxidation of Aromatics in Enantiocontrolled Synthesis .1. Expedient and General AsymmetricSynthesis of Inositols and Carbohydrates Via an Unusual Oxidation of a Polarized Diene with Potassium Permanganate," *J. Chem. Soc. Perkin Trans.*, 1: 1553-1567.
Huntley, "Speckle photography fringe analysis: assessment of current algorithms," Applied Optics, vol. 28:4316 (1989).
Jacobson SC, et al., "Fused Quartz Substrates for Microchip Electrophoresis," *Analytical Chemistry*, 67: 2059-2063 (1995).
Jacobson SC, et al., "Microfluidic devices for electrokinetically driven parallel and serial mixing," *Analytical Chemistry*, 71: 4455-4459 (1999).
Kabanov AV, et al., "A new class of antivirals: antisense oligonucleotides combined with a hydrophobic substituent effectively inhibit influenza virus reproduction and synthesis of virus-specific proteins in MDCK cells," *FEBS Letters*, 259(2): 327-330 (1990).
Kalghatgi KK, et al., "Microbial L-phenylalanine ammonia-lyase. Purification, subunit structure and kinetic properties of the enzyme from Rhizoctonia sol ani," *Biochemical Journal*, 149: 65-75 (1975).
Kalinina, et al., "Nanoliter scale PCR with TaqMan detection," *Nucleic Acid Research*, 25(10):1999-2004 (1997).
Keen et al., "Rapid detection of single base mismatches as heteroduplexes on Hydrolink gels," *Trends Genet.*, 7: 5 (1991).
Kenmore CK, et al., "Refractive-index Detection by interferometric Backscatter in Packed-capillary High-performance Liquid Chromatography," *Journal of Chromatography A*, 762: 219225 (1997).
Kerker M,e t al., "Scattering of Electomagnetic Waves from Concentric Infinite Cylinders,"*Journal of the Optical Society of Americai*,51: 506-508 (1961).
Klee et al., "Purification of cyclic 3',5'-nucleotide phosphodiesterase inhibitory protein by affinity chromatography on activator protein couples to sepharose," Biochem 17:120-126 (1978).
Korbel GA, et al., "Reaction microarrays: a method for rapidly determining the enantiomeric excess of thousands of samples," *Journal of the American Chemical Society*, 123: 361-362.
Kuhlmann J, "Drug Research: From the Idea to the Product," *International Journal of Clinical Pharmacology and Therapeutics*, 541-552 (1997).
Kunkel TA, et al., "Rapid and efficient site-specific mutagenesis without phenotypic selection," *Methods Enzymol*, 154: 367-382 (1987).
Kussrow A, et al., "Measurement of Mono- and Polyvalent Carbohydrate-Lectin Binding by Back-Scattering Interferometry," *Anal. Chem.*, 81: 4889-4897 (2009).
Kussrow, "Interrogation of Biomolecular Interactions Utilizing Backscattering Interferometry," Dissertation, Vanderbilt University (2009), pp. i-xii and 1-115 (127 pages total), retrieved from http://etd.library.vanderbilt.edu/available/etd-12042009-092927 on Apr. 29, 2013.

(56) References Cited

OTHER PUBLICATIONS

Kussrow and Bornhop, "Characterizing Molecular Interaction," *Screening Trends in Drug Discovery*, pp. 14-16 (2009).

Lan et al., "Non-mechanical sub-pixel image shifter for acquiring super-resolution digital images," *Optics Express*, vol. 17:22992-23002 (2009).

Langone, "Protein A of *Staphylococcus aureus* and related immunoglobulin receptors produced by streptococci and pneumonococci," *Adv Immunol*, 32:157-252 (1982).

Latham et al., "Photobiotin surface chemistry improves label-free interferometric sensing of biochemical interactions," Angew Chem Int Ed, 45:955-958 (2006).

Letsinger, et al., "Cholesteryl-conjugated oligonucleotides: Synthesis, properties, and activity as inhibitors of replication of human immunodeficiency virus in cell culture," *Proc. Natl. Acad. Sci. USA*, 86: 6553-6556 (1989).

Liu SR, et al., "Optimization of high-speed DNA sequencing on microfabricated capillary electrophoresis channels," *Analytical Chemistry*, 71: 566-573 (1999).

Malacara D, et al., "Interferogram Analysis for Optical Testing," New York: Marcel Dekker, Inc (1998).

Manoharan M, et al., "Chemical modifications to improve uptake, and bioavailability of antisense oligonucleotides," *Ann. NY Acad. Sci.*, 660: 306-309 (1992).

Manoharan M, et al., "Cholic acid-oligonucleotide conjugates for antisense applications," *Biorg. Med. Chem. Lett.*, 4: 1053-1060 (1994).

Manoharan M, et al., Introduction of a Lipophilic Thioether Tether in the Minor Groove of Nucleic Acids for Antisense Applications, *Bioorg. Med. Chem. Lett.*, 3: 2765-2770 (1993).

Manoharan M, et al., "Lipidic nucleic acids," *Tetrahedron Lett.*, 36: 3651-3654 (1995).

Manoharan M, et al., "Oligonucleotide conjugates: alteration of the pharmacokinetic properties of antisense agents," *Nucleosides & Nucleotides*, 14: 969-973 (1995).

Manz A, et al., "Micromachining of Monocrystalline Silicon and Glass for Chemical-Analysis Systems—a Look into Next Century Technology or Just a Fashionable Craze," *Trac-Trends in Analytical Chemistry*, 10: 144-149 (1991).

Manz A, et al., "Miniaturized Total Chemical-Analysis Systems—a Novel Concept for Chemical Sensing," *Sensors and Actuators B-Chemical*, 1: 244-248 (1990).

Marcuse et al., "Light scattering from optical fibers with arbitrary refractive-index distributions," J Opt Soc Am, 65:367-375 (1975).

Marketwired, "Molecular Sensing, Inc. and VIB Enter Agreement in Alzheimer's Disease Research." Internet Publication http://www.marketwired.com/press-release/molecular-sensing-inc-and-vib-enter-agreement-in-alzheimers-disease-research-1231768.htm (2009).

Markov D, et al., "A Fourier Analysis Approach for Capillary Polarimetry," *Electrophoresis*, 23(5): 809-812 (2002).

Markov D, et al., "Breaking the 10-7 B arrier for RI Measurements in Nanoliter Volumes," *Analytical Chemistry*, 74: 5438-5441 (2002).

Markov D, et al., "Nanoliter-scale Non-invasive Flow-Rate Quantification using Micro-Interferometric Backscatter and Phase Detection," *Fresenius' Journal of Analytical Chemistry*, 371: 234-237 (2001).

Markov DA, et al., "Non-Invasive Fluid Flow Measurements in Microfluidic Channels with Backscatter Interferometry," *Electrophoresis* 25: 3805-3809 (2004).

Markov et al., "Label-Free Molecular Interaction Determinations with Nanoscale Interferometry," J Am Chem Soc 126:16659-16664 (2004).

Martynova L, et al., "Fabrication of plastic micro fluid channels by imprinting methods," *Analytical Chemistry*, 69: 4782-4789 (1997).

Mathworks, "Registering an Image Using Normalized Cross-Correlation," http://www.mathworks.com/products/demos/image/cross_correlation/imreg.html, last accessed May 15, 2014.

May O, et al., "Inverting enantioselectivity by directed evolution of hydantoinase for improved production ofL-methionine," *Nature Biotechnology*, 18: 317-320 (2000).

Maystre F, et al., "Enhanced Polarimetric Detection in Hplc Using a Refractive-Index Equalizer," *Analytical Chemistry*, 66: 2882-2887 (1994).

Miller MT, et al., "Structure of β-lactam synthetase reveals how to synthesize antibiotics instead of asparagine," *Nature Struct. Biol.*, 8: 684-689 (2001).

Miller MT, et al., "The catalytic cycle of β-lactam synthetase observed by x-ray crystallographic snapshots," *Proc. Nat. Acad. Sci. USA*, 99: 14752-14757 (2002).

Miroshnikova et al., "Percussion hole drilling of metals with a fourth-harmonic Nd:YAG laser studied by defocused laser speckle correlation," Applied Optics, vol. 44:3403 (2005).

Mishra RK, et al., "Improved leishmanicidal effect of phosphorotioate antisense oligonucleotides by LDL-mediated delivery," *Biochim Biophys Acta*, 1264: 229-327 (1995).

Molphy et al., "Surface Modification of Kaolin. 1. Covalent Attachement of Polyethylene Glycol using a Urethane Linker," *Polymer International*, 34: 425-431 (1994).

Montigiani et al., "Alanine substitutions on calmodulin-binding peptides result in unexpected affinity enhancement," *J Mol Biol* 258:6-13 (1996).

Morrison, et al., "Nanoliter high throughput quantitative PCR," Nucleic Acid Res, 34(18):e123 (2004).

Neifeld, "Information, resolution, and space-bandwidth product," Optics Letters, vol. 23:1477-1479 (1998).

Nielson PE, et al., "Sequence-selective recognition of DNA by strand displacement with a thymine-substitued polyamide," *Science*, 254: 1497-1500 (1991).

Oberhauser B, et al, "Effective incorporation of 2'-O-methylobligoribonucleotides into liposomes and enhanced cell association through modification with thiocholesterol," *Nucleic Acids Research*, 20(3): 533-538 (1992).

Orita et al., "Rapid and sensitive detection of point mutations and DNA polymorphisms using the polymerase chain reaction," *Genomics*, 5: 874-879 (1989).

Persson et al., "Lipid-Based Passivation in Nanofluidics," *Nano Letters*, 12: 2260-2265.

Pitter et al., "Focus errors and their correction in microscopic deformation analysis using correlation," Optics Express, vol. 10:1361-1367 (2002).

Porat B, "A Course in Digital Signal Processing," New York: Wiley and Sons (1997).

Quake SR, et al., "From micro- to nanofabrication with soft materials," *Science*, 290: 1536-1540 (2000).

Read, et al., "Aseptic meningitis and encephalitis: the role of PCR in the diagnostic laboratory," Clin Microbiol, 35:691-696 (1997).

Reem et al, "Induction and upregulation by interleukin 2 of high-affinity interleukin 2 receptors on thymocytes and T cells," Proc Natl Acad Sci USA, 82:8663-8666 (1985).

Reetz MT, "Combinatorial and evolution-based methods in the creation of enantioselective catalysts," *Angewandte Chemie-International Edition*, 40: 284-310 (2001).

Reetz MT, "New methods for the high-throughput screening of enantioselective catalysts and biocatalysts," *Angewandte Chemie-International Edition*, 41: 1335-1338 (2002).

Resetar S, et al., "Anticipating Technological Change: Combinatorial Chemistry and the Environment," *EPA* (2001).

Rich et al., "High-resolution and high-throughput protocols for measuring drug/human serum albumin interactions using BIACORE," *Anal Biochem* 296:197-207 (2001).

Rother D, et al., "An active site homology model of phenylalanine ammonia-lyase from Petroselinum crispum," *European Journal of Biochemistry*, 269: 3065-3075 (2002).

Rouhi AM, "Chiral chemistry," *Chemical & Engineering News*, 82: 47 (2004).

Rouhi Am, "Taking a measure of chiral riches—Researchers respond to high demand for ways to measure enantioenrichment quickly," *Chemical & Engineering News*, 80: 51 (2002).

(56) References Cited

OTHER PUBLICATIONS

Rouhi Am, "Chiral roundup—As pharmaceutical companies face bleak prospects, their suppliers diligently tend the fertile fields of chiral chemistry in varied ways," *Chemical & Engineering News*, 80: 43 (2002).

Rudolph Research Analytical, "Polarimetry," webpage retried from www.rudolphresearch.com/polarimetry.htm (last accessed Aug. 3, 2009).

Rychlik W, et al., "New algorithm for determining primer efficiency in PCR and sequencing," *J. NIH Res.*, 6: 78 (1994).

Saha et al., "Comparative study of IgG binding to proteins G and A: Nonequilibrium kinetic and binding constant determination with the acoustic waveguide device," *Anal Chem*, 75:835-842 (2003).

Saison-Behmoaras T, et al., "Short modified antisense oligonucleotides directed against ha-*ras* point mutations induce selective cleavage of the messenger RNA and inhibit T24 cell proliferation," *EMGO J.*, 10: 1111-1118 (1991).

Schipper EF, et al., "The Waveguide Mach-Zender Interferometer as Atrazine Sensor," *Analytical Chemistry*, 70: 1192-1197 (1998).

Schonfeld DL, et al., "Polarimetric assay for the medium-throuput determination of alpha-amino acid racemase activity," *Analytical Chemistry*, 76: 1184-1188 (2004).

Schuster B, et al., "The Mechanism of Action of Phenylalanine Ammonia-Lyase—the Role of Prosthetic Dehydroalanine," *Proceedings of the National Academy of Sciences of the United States of America*, 92: 8433-8437 (1995).

Shea RG, et al., "Synthesis, hybridization properties and antiviral activity of lipid-oligodeoxynucleotide conjugates," *Nucl. Acids Res.*, 8: 3777-3783 (1990).

Sidick et al., "Adaptive cross-correlation algorithm for extended scene Shack-Hartmann wavefront sensing," *Optics Letters*, vol. 33:213-215 (2008).

Sjodahl et al., "Electronic speckle photography: analysis of an algorithm giving the displacement with subpixel accuracy," *Applied Optics*, vol. 32:2278-2284 (1993).

Sjodahl et al., "Measurement of shape by using projected random patterns and temporal digital speckle photography," *Applied Optics*, vol. 38:1990-1997 (1999).

Sjodahl, "Accuracy in electronic speckle photography," *Applied Optics*, vol. 36:2875-2885 (1997).

Sjodahl, "Electronic speckle photography: increased accuracy by nonintegral pixel shifting," *Applied Optics*, vol. 33:6667-6673 (1994).

Sorensen HS, "Self Calibrating Interferometric Sensor," PhD thesis Riso-PhD-19(EN), Riso National Laboratory, Denmark, Jan. 2006, pp. 1-145.

Sorenson HS, et al., "Highly sensitive biosensing based on interference from light scattering in capillary tubes," *Applied Physics Letters*, 89(15) (2006).

Sorensen HS, et al., "Absolute refractive index determination by microinterferometric backscatter detection," *Analytical Chemistry*, 75: 1946-1953 (2003).

Soumet, et al., "Identification by a multiplex PCR-based assay of *Salmonella typhimurium* and *Salmonella enteritidis* strains from environmental swabs of poultry houses ," Lett Appl Microbiol, 29(1) 1-6 (1999).

Speaker, et al., "Characterization of a calmodulin-binding protein that is deficient in trifluoperazine-resistant variants of the macrophage-like cell line J774," Proc Natl Acad Sci USA, 80:329-333 (1983).

St. Claire JC, "Heat Index Flow Monitoring in Capillaries with Interferometric Backscatter Detection," *Analytical Chemistry*, 72(19): 4726-4730 (2000).

STN Entry retrieved from STN Oct. 10, 2013 p. 1.

Suzuki, et al., "Planar lipid bilayer reconstitution with a microfluidic system," *Lab Chip*, 4: 502-505 (2004).

Svanbro et al., "Complex amplitude correlation for compensation of large in-plane motion in digital speckle pattern interferometry," *Applied Optics*, vol. 45:8641-8647 (2006).

Svinarchuk FP, et al., "Inhibition of HIV proliferation in MT-4 cells by antisense oligonucleotide conjugated to lipophilic groups," *Biochimi*, 75(1-2): 49-54 (1993).

Swinney K and Bornhop DJ, "Detection in Capillary Electrophoresis: A Review," *Electrophoresis*, 21: 1239-1250 (2000).

Swinney K, et al., "Capillary-Scale Polarimetry for Flowing Streams," *Analyst*, 126: 673-675 (2001).

Swinney K, et al., "Chip-Scale Universal Detection Based on Backscatter Interferometry," *Analytical Chemistry*, 72: 2690-2695 (2000).

Swinney K, et al., "A chip-scale universal detector for electrophoresis based on backscattering interferometry," *Analyst*, 125: 1713-1717 (2000).

Swinney K, et al., "D-β-Hydroxybutrate Reaction Kinetics Studied in Nanoliter Volumes using a Capillary Polarimeter," *Applied Spectroscopy*, 54: 1458-1469 (2000).

Swinney K, et al., "Ion Analysis Using Capillary Electrophoresis with Refractive Index Detection," *Microchemical Journal*, 62: 154-163 (1999).

Swinney K, et al., "Laser-Based Capillary Polarimetry," *J. Capillary Electrophoresis and Microchip Technology*, 6: 93-96 (1999).

Swinney K, et al., "Micro-interferometric backscatter detection using a diode laser," *Analytica Chimica Acta*, 400: 265-280 (1999).

Swinney K, et al., "Nanoliter Volume Polarimetry," *Applied Spectroscopy*, 56(1): 134-138 (2002).

Swinney K, et al., "Non-Invasive Picoliter Volume Thermometry Based on Backscatter Interferometry," *Electrohporesis*, 22: 2032-2036 (2001).

Swinney K, et al., "Quantification and Evaluation of Joule Heating in On-Chip CE," *Electrophoresis*, 23(4): 621-625 (2002).

Swinney K, et al., "Ultrasmall Volume refractive index detection using microinterferometry," *Review of Scientific Instruments*, 71: 2684-2692 (2000).

Swinney K, et al., "Universal Detection in Capillary Electrophoresis by Micro-Interferometric Backscatter," *Analyst*, 124: 221-226 (1999).

Swinney K,e t al., "Universal Detection for Capillary Electrophoresis—Using Micro-Interferometric Backscatter Detection," *J. MicroColumn Separation*, 11: 596-604 (1999).

Swinney, et la., "A Review of CE Detection Methodologies," *CRC Critical Reviews in Analytical Chemistry*, 30(1): 1-30.

Synnergren et al. "Optical in-plane strain field sensor," *Applied Optics*, vol. 41:1323-1329 (2002).

Synnergren et al., "Application of digital speckle photography to flash x-ray studies of internal deformation fields in impact experiments," *Applied Optics*, vol. 36:4030-4036 (1999).

Synnergren et al., "Digital speckle photography: visualization of mesoflow through clustered fiber networks," *Applied Optics*, vol. 41:1368-1373 (2002).

Takushima et al., "Optical reflectometry based on correlation detection and its application to the in-service monitoring of WDM passive optical network," *Optics Express*, vol. 15:5318-5326 (2007).

Tan AM, et al., "Rapid fabrication of microfluidic devices in poly(dimethylsiloxane) by photocopying," *Lab on a Chip*, 1: 7-9 (2001).

Tarigan H, et al., "Capillary-Scale Refractive Index Detection by Interferometric Backscatter," *Analytical Chemistry*, 68: 1762-1770 (1996).

Theze, et al., "Interleukin 2 and its receptors: recent advances and new immunological functions," *Immunology Today* 17:481-486 (1996).

Török, "Calmodulin conformational changes in the activation of protein kinases," *Biochem Soc Trans* 30:55-61 (2002).

Tsukamoto M, et al., "Recent advances in the measurement of enantiomeric excesses," *Advanced Synthesis & Catalysis*, 344: 453-463.

Van Delden RA, et al., "Color indicators of molecular chirality based on doped liquid crystals," *Angewandte Chemie-International Edition*, 40: 3198 (2001).

Veldhuis GJ, et al., "Highly-sensitive Passive Integrated Optical Spiral-Shaped Waveguide Refractometer," *Applied Physics Letters*, 71(20): 2895-2897 (1997).

(56) References Cited

OTHER PUBLICATIONS

Viola et al., "Alignment by maximization of mutual information", International Conference on Computer Vision (E. Grimson, S. Shafer, A. Blake and K. Sugihara, eds.), IEEE Computer Society Press, Los Alamitos, CA, pp. 16-23, 1995.

Vogelstein, et al., "Digital PCR," *Proc Natl Acad Sci USA*, 96(16):9236-9241 (1999).

Volanthen M, et al., "Multiplexed optical fibre strain sensing using cross-correlation of subcarrier interferometric spectra," *Electronics Letters*, IEE Stevenage, GB, 32(3): 243-244 (1996).

Wang et al., "Pseudophase information from the complex analytic signal of speckle fields and its applications. Part I: Microdisplacement observation based on phase-only correlation in the signal domain," Applied Optics, vol. 44:4909-4915 (2005).

Wang et al.,"Optical vortex metrology for nanometric speckle displacement measurement," Optics Express, vol. 14:120-127 (2006).

Wang Z, et al., "Attomole Sensitivity for Proteins and Polypeptides with On-chip CE and Universal Detection by Interferometric Backscatter," *Electrophoresis*, 24(5): 865-873 (2003).

Wang, et al., "High-speed digital-image correlation method," Optics Letters, vol. 34:1955-1957 (2009).

Watkins, "Scattering from side-illuminated clad glass fibers for determination of fiber parameters," *J Opt Soc Am*, 64:767-772 (1974).

Wetmur JG, et al., "DNA Probes: Applications of the Principles of Nucleic Acid Hybridization," *Crit. Rev. Biochem. Mol. Biol.*, 26: 227-259 (1991).

Whitesides et al., "Soft lithography in biology and biochemistry," *Annu Rev Biomed Eng*, 3:335-373 (2001).

Wu ZY, et al., "Polymer microchips bonded by O-2-plasma activation," *Electrophoresis*, 23: 782-790 (2002).

Yamaguchi, "Fringe formation in speckle photography," J. Opt. Soc. Am. A, vol. 1:81-86 (1984).

Yanik, et al., Development of a New Laser Based Polarimetric Detector and Its Application to High-performance Liquid Chromatography. PDR-Chiral, 1998.

Yeung, et al., "Electrochemistry-Based Real-Time PCR on a Microchip," *Anal Chem*, 80:363-368 (2008).

Ymeti, et al., "Realization of a multichannel integrated young interferometer chemical sensor," *Applied Optics*, 42: 5649-5660 (2003).

Young, et al., "Novel Recombinant-Antigen Enzyme Immunoassay for Serological Diagnosis of Syphilis," *J Clin Microbio*, 36(4):913-917 (1998).

Yu et al., "Interaction of an artificial antimicrobial peptide with lipid membranes," *Biochemica et Biophysica Acta*, 1788: 333-344 (2009).

Yu et al., "Energy landscape of aptamer/protein complexes studies by single-molecule force spectroscopy," *Chem Asian J*, 2:284-289 (2007).

Zandonella C, "Cell nanotechnology: The tiny toolkit," *Nature*, 423: 10-12 (2003).

Zazopoulos E, et al., "A genomics-guided approach for discovering and expressing cryptic metabolic pathways," *Nature Biotech.*, 21: 187-190 (2003).

Zhang et al., "Proteins and cells on PEG immovilized silicon surfaces," *Biomaterials*, 19: 953-960.

Zhihong et al., "A new sandwich-type assay of estrogen using piezoelectric biosensor immobilized with estrogen response element," Anal Commun, 36:281-283 (1999).

Zhou J, et al., "Spectroscopic studies of substrate interactions with clavaminate synthase 2, a multifunctional a-KG-dependent non-heme iron enzyme: Correlation with mechanisms and reactivities," *J. Am. Chem. Soc.*, 123: 7388-7398(2001).

Zhou JM, et al., "Spectroscopic studies of substrates and cosubstrate binding to the a-ketoglutarate-dependent non-heme iron enzyme clavaminate synthase 2: correlation to reactivities and mechanisms," *Journal of Inorganic Biochemistry*, 74: 350-350 (1999).

Zhou JM, et al., "Substrate binding to the β-keoglutarate-dependent non-heme iron enzyme clavaminate synthase 2: Coupling mechanism of oxidative decarboxylation and hydroxylation," J. Am. Chem. Soc., 120: 13539-13540 (1998).

Issue Notification issued on Feb. 22, 2012 for U.S. Appl. No. 11/666,046, filed Jul. 24, 2009 (Applicant—Vanderbilt University // Inventors—Bornhop et al.) (1 page).

Notice of Allowance issued Nov. 3, 2011 for U.S. Appl. No. 11/666,046, filed Jul. 24, 2009 (Applicant—Vanderbilt University // Inventors—Bornhop et al.) (8 pages).

Examiner-Initiated Interview Summary issued on Nov. 3, 2011 for U.S. Appl. No. 11/666,046, filed Jul. 24, 2009 (Applicant—Vanderbilt University // Inventors—Bornhop et al.) (1 page).

Issue Notification issued on Oct. 27, 2010 for U.S. Appl. No. 12/122,175, filed May 16, 2008 (Applicant—Vanderbilt University // Inventors—Jones et al.) (1 page).

Notice of Allowance issued Sep. 10, 2010 for U.S. Appl. No. 12/122,175, filed May 16, 2008 (Applicant—Vanderbilt University // Inventors—Jones et al.) (4 pages).

Notice of Allowance issued Jul. 22, 2010 for U.S. Appl. No. 12/122,175, filed May 16, 2008 (Applicant—Vanderbilt University // Inventors—Jones et al.) (7 pages).

Response to Office Action filed Jun. 29, 2010 for U.S. Appl. No. 12/122,175, filed May 16, 2008 (Applicant—Vanderbilt University // Inventors—Jones et al.) (17 pages).

Non-Final Rejection issued on Apr. 28, 2010 for U.S. Appl. No. 12/122,175, filed May 16, 2008 (Applicant—Vanderbilt University // Inventors—Jones et al.) (5 pages).

Issue Notification issued on May 1, 2013 for U.S. Appl. No. 12/674,610, filed Oct. 4, 2011 (Applicant—Vanderbilt University // Inventors—Bornhop et al.) (1 page).

Notice of Allowance issued Mar. 20, 2013 for U.S. Appl. No. 12/674,610, filed Oct. 4, 2011 (Applicant—Vanderbilt University // Inventors—Bornhop et al.) (10 pages).

Response to Office Action filed Dec. 7, 2012 for U.S. Appl. No. 12/674,610, filed Oct. 4, 2011 (Applicant—Vanderbilt University // Inventors—Bornhop et al.) (13 pages).

Non-Final Rejection issued Jun. 7, 2012 for U.S. Appl. No. 12/674,610, filed Oct. 4, 2011 (Applicant—Vanderbilt University // Inventors—Bornhop et al.) (21 pages).

Election Under Restriction Requirement filed Feb. 18, 2012 for U.S. Appl. No. 12/674,610, filed Oct. 4, 2011 (Applicant—Vanderbilt University // Inventors—Bornhop et al.) (10 pages).

Requirement for Restriction/Election issued Dec. 19, 2011 for U.S. Appl. No. 12/674,610, filed Oct. 4, 2011 (Applicant—Vanderbilt University // Inventors—Bornhop et al.) (12 pages).

Preliminary Amendment filed Oct. 4, 2011 for U.S. Appl. No. 12/674,610, filed Oct. 4, 2011 (Applicant—Vanderbilt University // Inventors—Bornhop et al.) (9 pages).

Issue Notification issued Feb. 1, 2012 for U.S. Appl. No. 12/331,354, filed Dec. 9, 2008 (Applicant—Vanderbilt University // Inventors—Bornhop et al.) (1 page).

Notice of Allowance issued Oct. 11, 2011 for U.S. Appl. No. 12/331,354, filed Dec. 9, 2008 (Applicant—Vanderbilt University // Inventors—Bornhop et al.) (7 pages).

Applicant Initiated Interview Summary (PTOL-413) issued Sep. 22, 2011 for U.S. Appl. No. 12/331,354, filed Dec. 9, 2008(Applicant—Vanderbilt University // Inventors—Bornhop et al.) (3 pages).

Response to Office Action filed Sep. 21, 2011 for U.S. Appl. No. 12/331,354, filed Dec. 9, 2008 (Applicant—Vanderbilt University // Inventors—Bornhop et al.) (14 pages).

Non-Final Rejection issued on Mar. 24, 2011 for U.S. Appl. No. 12/331,354, filed Dec. 28, 2008 (Applicant—Vanderbilt University // Inventors—Bornhop et al.) (15 pages).

Response to Restriction Requirement filed Jan. 20, 2011 for U.S. Appl. No. 12/331,354, filed Dec. 9, 2008 (Applicant—Vanderbilt University // Inventors—Bornhop et al.) (9 pages).

Requirement for Restriction/Election issued Dec. 28, 2010 for U.S. Appl. No. 12/331,354, filed Dec. 9, 2008 (Applicant—Vanderbilt University // Inventors—Bornhop et al.) (12 pages).

Preliminary Amendment filed Jun. 5, 2009 for U.S. Appl. No. 12/331,354, filed Dec. 9, 2008 (Applicant—Vanderbilt University // Inventors—Bornhop et al.) (4 pages).

(56) References Cited

OTHER PUBLICATIONS

Final Rejection issued Aug. 21, 2012 for U.S. Appl. No. 12/655,899, filed Jan. 8, 2010 (Applicant—Vanderbilt University // Inventors—Weinberger et al.) (18 pages).
Applicant Initiated interview Summary (PTOL-413) issued Jul. 23, 2012 for U.S. Appl. No. 12/655,899, filed Jan. 8, 2010 (Applicant—Vanderbilt University // Inventors—Weinberger et al.) (3 pages).
Response to Non-Final Rejection issued on Jul. 23, 2012 for U.S. Appl. No. 12/655,899, filed Jan. 8, 2010 (Applicant—Vanderbilt University // Inventors—Weinberger et al.) (11 pages).
Non-Final Rejection issued Feb. 21, 2012 for U.S. Appl. No. 12/655,899, filed Jan. 8, 2010 (Applicant—Vanderbilt University // Inventors—Weinberger et al.) (20 pages).
Election and Preliminary Amendment filed Dec. 19, 2011 for U.S. Appl. No. 12/655,899, filed Jan. 8, 2010 (Applicant—Vanderbilt University // Inventors—Weinberger et al.) (5 pages).
Requirement for Restriction/Election issued Oct. 18, 2011 for U.S. Appl. No. 12/655,899, filed Jan. 8, 2010 (Applicant—Vanderbilt University // Inventors—Weinberger et al.) (10 pages).
Preliminary Amendment filed Jul. 12, 2010 for U.S. Appl. No. 12/655,899, filed Jan. 8, 2010 (Applicant—Vanderbilt University // Inventors—Weinberger et al.) (3 pages).
Notice of Allowance issued on May 28, 2004 for U.S. Appl. No. 10/053,877, filed Jan. 24, 2002 (Applicant—Vanderbilt University // Inventors—Bornhop et al.) (7 pages).
Amendment after Notice of Allowance filed on Feb. 19, 2004 for U.S. Appl. No. 10/053,877, filed Jan. 24, 2002 (Applicant—Vanderbilt University // Inventors—Bornhop et al.) (8 pages).
Notice of Allowance issued on Nov. 20, 2003 for U.S. Appl. No. 10/053,877, filed Jan. 24, 2002 (Applicant—Vanderbilt University // Inventors—Bornhop et al.) (7 pages).
Response to Non-Final Rejection filed Oct. 1, 2003 for U.S. Appl. No. 10/053,877, filed Jan. 24, 2002 (Applicant—Vanderbilt University // Inventors—Bornhop et al.) (2 pages).
Non-Final Rejection issued on Jul. 8, 2003 for U.S. Appl. No. 10/053,877, filed Jan. 24, 2002 (Applicant—Vanderbilt University // Inventors—Bornhop et al.) (6 pages).
Non-Final Rejection issued Oct. 2, 2012 for U.S. Appl. No. 13/157,803, filed Jun. 10, 2011 (Applicant—Vanderbilt University // Inventors—Bornhop et al.) (17 pages).
Response to Office Action filed Feb. 4, 2013 for U.S. Appl. No. 13/157,803, filed Jun. 10, 2011 (Applicant—Vanderbilt University // Inventors—Bornhop et al.) (10 pages).
Non-Final Rejection issued Mar. 19, 2013 for U.S. Appl. No. 13/157,803, filed Jun. 10, 2011 (Applicant—Vanderbilt University // Inventors—Bornhop et al.) (16 pages).
Response to Office Action filed Jul. 19, 2013 for U.S. Appl. No. 13/157,803, filed Jun. 10, 2011 (Applicant—Vanderbilt University // Inventors—Bornhop et al.) (11 pages).
Final Rejection issued on Aug. 22, 2013 for U.S. Appl. No. 13/157,803, filed Jun. 10, 2011 (Applicant—Vanderbilt University // Inventors—Bornhop et al.) (17 pages).
Applicant Initiated Interview Summary (PTOL-413) issued on Dec. 2, 2013 for U.S. Appl. No. 13/157,803, filed Jun. 10, 2011 (Applicant—Vanderbilt University // Inventors—Bornhop et al.) (3 pages).
Request for Continued Examination filed on Jan. 22, 2014 for U.S. Appl. No. 13/157,803, filed Jun. 10, 2011 (Applicant—Vanderbilt University // Inventors—Bornhop et al.) (15 pages).
Non-Final Rejection issued Jul. 23, 2014 for U.S. Appl. No. 13/157,803, filed Jun. 10, 2011 (Applicant—Vanderbilt University // Inventors—Bornhop et al.) (17 pages).
Response to Non-Final Office action filed Oct. 23, 2014 for U.S. Appl. No. 13/157,803, filed Jun. 10, 2011 (Applicant—Vanderbilt University // Inventors—Bornhop et al.) (12 pages).
Final Office action issued Dec. 9, 2014 for U.S. Appl. No. 13/157,803, filed Jun. 10, 2011 (Applicant—Vanderbilt University // Inventors—Bornhop et al.) (19 pages).
Request for Continued Examination and Applicants Arguments/Remarks mailed Jun. 9, 2015 for U.S. Appl. No. 13/157,803, filed Jun. 10, 2011 (Applicant—Vanderbilt University // Inventors—Bornhop et al.) (11 pages).
Preliminary Amendment filed Apr. 15, 2013 for U.S. Appl. No. 13/879,523, filed Jun. 28, 2013 (Applicant—Vanderbilt University // Inventors—Bornhop et al.) (7 pages).
Restriction Requirement issued Jun. 2, 2015 for U.S. Appl. No. 13/879,523, filed Jun. 28, 2013 (Applicant—Vanderbilt University // Inventors—Bornhop et al.) (7 pages).
Non-Final Rejection issued Jan. 2, 2014 for U.S. Appl. No. 13/409,557, filed Mar. 1, 2012 (Applicant—Vanderbilt University // Inventors—Bornhop et al.) (35 pages).
Response to Non-Final Office Action filed Oct. 7, 2013 for U.S. Appl. No. 13/409,557, filed Mar. 1, 2012 (Applicant—Vanderbilt University // Inventors—Bornhop et al.) (9 pages).
Non-Final Rejection issued May 6, 2013 for U.S. Appl. No. 13/409,557, filed Mar. 1, 2012 (Applicant—Vanderbilt University // Inventors—Bornhop et al.) (19 pages).
Response to Restriction Requirement filed Mar. 7, 2013 for U.S. Appl. No. 13/409,557, filed Mar. 1, 2012 (Applicant—Vanderbilt University // Inventors—Bornhop et al.) (2 pages).
Restriction Requirement issued Jan. 7, 2013 for U.S. Appl. No. 13/409,557, filed Mar. 1, 2012 (Applicant—Vanderbilt University // Inventors—Bornhop et al.) (6 pages).
Non-Final Office Action issued on Mar. 2, 2015 for U.S. Appl. No. 13/892,642, filed May 13, 2013 and published as US-2013-0301055-A1 on Nov. 14, 2013 (Inventor—Bornhop et al. // Applicant—Vanderbilt University) (13 pages).
International Preliminary Report on Patentability issued on Apr. 27, 2007 for PCT/US2005/38168 filed Oct. 24, 2005 and published as WO 2006/047408 on May 4, 2006 (Applicants—Vanderbilt University // Inventors—Bornhop et al.) (6 pages).
International Search Report and Written Opinion mailed on Apr. 26, 2006 for PCT/US2005/38168 filed Oct. 24, 2005 and published as WO 2006/047408 on May 4, 2006 (Applicants—Vanderbilt University // Inventors—Bornhop et al.) (1 page).
Supplementary International Search Report mailed on May 16, 2012 for PCT/US2005/38168 filed Oct. 24, 2005 and published as WO 2006/047408 on May 4, 2006 (Applicants—Vanderbilt University // Inventors—Bornhop et al.) (6 pages).
International Preliminary Examination Report issued Jun. 8, 2010 for PCT/US2000/020783 filed Aug. 17, 2000 and published as WO 2001/014858 on Mar. 1, 2001 (Applicant—Texas Tech University Health Sciences Center // Inventors—Bornhop et al.) (5 pages).
International Preliminary Report on Patentability issued Nov. 24, 2009 for US/PCT/2008/063879 filed May 16, 2008 and published as WO 2008/144496 on Nov. 27, 2008 (Applicant—Vanderbilt University // Inventors—Jones et al.) (10 pages).
International Search Report mailed Aug. 19, 2008 for US/PCT/2008/063879 filed May 16, 2008 and published as WO 2008/144496 on Nov. 27, 2008 (Applicant—Vanderbilt University // Inventors—Jones et al.) (2 pages).
Supplementary International Search Report mailed Oct. 5, 2012 for US/PCT/2008/063879 filed May 16, 2008 and published as WO 2008/144496 on Nov. 27, 2008 (Applicant—Vanderbilt University // Inventors—Jones et al.) (8 pages).
International Preliminary Report on Patentability issued Mar. 24, 2010 for PCT/US2008/077145 filed Sep. 20, 2008 and published as WO 2009/039466 on Mar. 26, 2009 (Applicant—Vanderbilt University // Inventors—Bornhop et al.) (9 pages).
International Search Report mailed Dec. 8, 2008 for PCT/US2008/077145 filed Sep. 20, 2008 and published as WO 2009/039466 on Mar. 26, 2009 (Applicant—Vanderbilt University // Inventors—Bornhop et al.) (1 page).
International Preliminary Report on Patentability issued Jul. 12, 2011 for ; PCT/US2010/000047 filed Jan. 8, 2010 and published as WO 2010/080710 on Jul. 15, 2010 (Applicants—Molecular Sensing, Inc. et al. // Inventors—Weinberger et al.) (5 pages).
International Search Report mailed Sep. 30, 2010 for PCT/US2010/000047 filed Jan. 8, 2010 and published as WO 2010/080710 on Jul. 15, 2010 (Applicants—Molecular Sensing, Inc. et al. // Inventors—Weinberger et al.) (3 pages).

(56) References Cited

OTHER PUBLICATIONS

Written Opinion mailed Sep. 30, 2010 for PCT/US2010/000047 filed Jan. 8, 2010 and published as WO 2010/080710 on Jul. 15, 2010 (Applicants—Molecular Sensing, Inc. et al. // Inventors—Weinberger et al.) (4 pages).
International Preliminary Report on Patentability issued Dec. 14, 2012 for PCT/US2011/039982 filed Jun. 10, 2011 and published as WO 2011/156713 on Dec. 15, 2011 (Applicants—Vanderbilt University // Inventors—Bornhop et al.) (5 pages).
International Search Report mailed Oct. 5, 2011 for PCT/US2011/039982 filed Jun. 10, 2011 and published as WO 2011/156713 on Dec. 15, 2011 (Applicants—Vanderbilt University // Inventors—Bornhop et al.) (2 pages).
Written Opinion mailed Oct. 5, 2011 for PCT/US2011/039982 filed Jun. 10, 2011 and published as WO 2011/156713 on Dec. 15, 2011 (Applicants—Vanderbilt University // Inventors—Bornhop et al.) (4 pages).
International Preliminary Report on Patentability issued Apr. 16, 2013 for PCT/US2011/056171 filed Oct. 13, 2011 and published as WO 2012/051429 on Apr. 19, 2012 (Applicants—Vanderbilt University // Inventors—Bornhop et al.) (7 pages).
International Search Report mailed Mar. 8, 2012 for PCT/US2011/056171 filed Oct. 13, 2011 and published as WO 2012/051429 on Apr. 19, 2012 (Applicants—Vanderbilt University // Inventors—Bornhop et al.) (2 pages).
Written Opinion mailed Mar. 8, 2012 for PCT/US2011/056171 filed Oct. 13, 2011 and published as WO 2012/051429 on Apr. 19, 2012 (Applicants—Vanderbilt University // Inventors—Bornhop et al.) (6 pages).
Supplementary European Search Report issued Jun. 1, 2012 for European Pat. App.No. ; 05821243.2 filed Oct. 24, 2005 (Applicant—Vanderbilt University // Inventors—Bornhop et al.) (6 pages).
Supplementary European Search Report issued Feb. 10, 2006 for European Pat. App. No. 00959154.6 filed Aug. 17, 2000 (Applicant—Texas Tech University Health Sciences Center // Inventors—Bornhop et al.) (3 pages).
Supplementary European Search Report issued Oct. 19, 2012 for European Pat. App. No. 08755681.7 filed May 16, 2008 (Applicant—Vanderbilt University // Inventors—Jones et al.) (8 pages).
Non-Final Rejection issued Nov. 23, 2015 for U.S. Appl. No. 13/157,803, filed Jun. 10, 2011 (Applicant—Vanderbilt University II Inventors—Bornhop et al.) (18 pages).
International Search Report and Written Opinion issued Mar. 24, 2016 for International Patent Application No. PCT/US2016/014439, which was filed on Jan. 22, 2016 (Inventor—Bornhop et al; Applicant—Vanderbilt University) (13 pages).
Non-Final Rejection was issued on Aug. 11, 2016 by the U.S. Patent and Trademark Office for U.S. Appl. No. 13/857,953, filed Apr. 5, 2013 and published as US-2013-0309661-A1 on Nov. 21, 2013 (Inventor—Darryl J. Bornhop; Applicant—Vanderbilt University) (15 pages).
Final Rejection was issued on Jun. 15, 2016 by the U.S. Patent and Trademark Office for U.S. Appl. No. 13/157,803, filed Jun. 10, 2011 and published as US 2012-0019834 A1 on Jan. 26, 2012 (Inventor—Darryl J. Bornhop; Applicant—Vanderbilt University) (19 pages).

* cited by examiner

--Prior Art--

NONAQUEOUS BACKSCATTERING INTERFEROMETRIC METHODS

STATEMENT OF GOVERNMENT SUPPORT

This Application claims the benefit of U.S. Provisional Application No. 61/445,352, filed on Feb. 22, 2011, which is incorporated herein by reference in its entirety.

BACKGROUND

Technical Field

The present disclosure related to analysis methods, and specifically to backscattering interferometric analysis methods and devices for use therewith.

Technical Background

Capillary-based analysis schemes, biochemical analysis, basic research in the biological sciences such as localized pH determinations in tissues and studies in protein folding, detection and study of microorganisms, and the miniaturization of instrumentation down to the size of a chip all require small volume detection. With the advent of lasers, light sources possessing unique properties including high spatial coherence, monochromaticity and high photon flux, unparalleled sensitivity and selectivity in chemical analysis has become possible; these technologies, however, can be both expensive and difficult to implement. In contrast, refractive index (RI) detection has been successfully applied to several small volume analytical separation schemes. For various reasons, RI detection represents an attractive alternative to fluorescence and absorbance: it is relatively simple, it can be used with a wide range of buffer systems, and it is universal, theoretically allowing detection of any solute, making it particularly applicable to solutes with poor absorption or fluorescence properties.

Recently developed methods utilizing refractive indices have been useful for measurements in aqueous systems, for example, to monitor biological interactions, but have been unable to monitor chemical phenomena in non-aqueous systems.

Accordingly, there is a need in the art for methods, systems, and apparatuses that can provide refractive index related measurements in non-aqueous systems.

SUMMARY

As embodied and broadly described herein, the invention, in one aspect, relates to an interferometric detection system comprising a light beam that impinges two or more discrete zones along a channel.

In one aspect, the invention relates to a method for determining a characteristic property of a non-aqueous sample, comprising the steps of providing an apparatus adapted for performing light scattering interferometry, the apparatus comprising a substrate, a channel formed in the substrate capable of receiving a non-aqueous sample to be analyzed, a light source for generating a light beam, a photodetector for receiving scattered light and generating a plurality of intensity signals; and at least one signal analyzer capable of receiving the intensity signals and determining therefrom one or more characteristic properties of the non-aqueous sample; and interrogating the non-aqueous sample using light scattering interferometry.

It will be apparent to those skilled in the art that various devices may be used to carry out the systems, methods, apparatuses, or computer program products of the present invention, including cell phones, personal digital assistants, wireless communication devices, personal computers, or dedicated hardware devices designed specifically to carry out aspects of the present invention. While aspects of the present invention may be described and claimed in a particular statutory class, such as the system statutory class, this is for convenience only and one of skill in the art will understand that each aspect of the present invention can be described and claimed in any statutory class, including systems, apparatuses, methods, and computer program products.

Unless otherwise expressly stated, it is in no way intended that any method or aspect set forth herein be construed as requiring that its steps be performed in a specific order. Accordingly, where a method, system, or computer program product claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
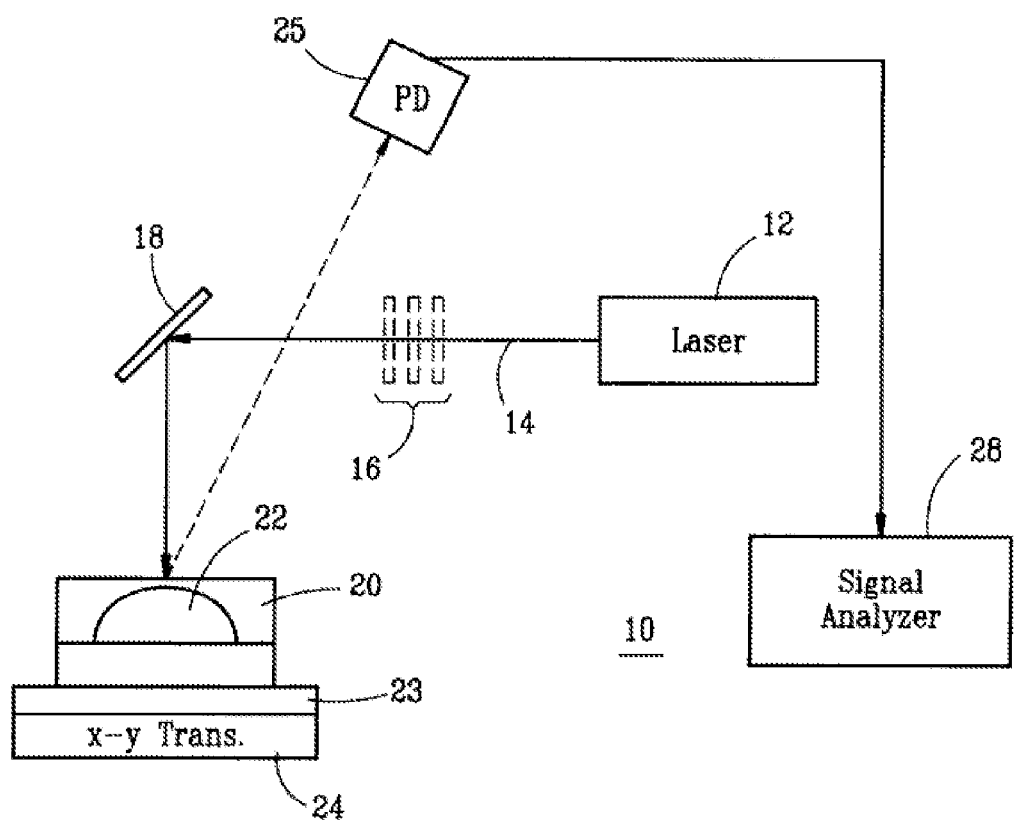
FIG. 1 is a schematic block diagram of a conventional backscattering interferometric detection system.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

DEFINITIONS

As used in the specification and the appended claims, the singular forms "a," "an" and "the" include plural referents unless the context clearly dictates otherwise. Thus, for example, reference to "a substrate," "a polymer," or "a sample" includes mixtures of two or more such substrates, polymers, or samples, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where the event or circumstance occurs and instances where it does not.

As used herein, the term "polymer" refers to a relatively high molecular weight organic compound, natural or synthetic (e.g., polyethylene, rubber, cellulose), whose structure can be represented by a repeated small unit, the monomer (e.g., ethane, isoprene, β-glucose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "bioassay" refers to a procedure for determining the concentration, purity, and/or biological activity of a substance.

As used herein, the term "chemical event" refers to a change in a physical or chemical property of an analyte in a sample that can be detected by the disclosed systems and methods. For example, a change in refractive index (RI), solute concentration and/or temperature can be a chemical event. As a further example, a biochemical binding or association (e.g., DNA hybridization) between two chemical or biological species can be a chemical event. As a further example, a disassociation of a complex or molecule can also be detected as an RI change. As a further example, a change in temperature, concentration, and association/dissociation can be observed as a function of time. As a further example, bioassays can be performed and can be used to observe a chemical event.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Back Scattering Interferometry

Rapid monitoring and detection of ultra small volume samples is in great demand. One analytical approach, Back-Scattering Interferometry (BSI), derives from the observation that coherent light impinging on a cylindrically shaped capillary produces a highly modulated interference pattern. Typically, BSI analyzes reflections from a capillary tube filled with a liquid of which one wants to measure the refractive index. The technique has been shown capable of measuring changes in refractive index of liquids on the order of $10^{-9}$. The BSI technique is a simple and universal method of detecting refractive index changes in small volumes of liquid and can be applied to monitor changes in concentrations of solutes, flow rates and temperature, all conducted in nanoliter volumes.

The BSI technique is based on interference of laser light after it is reflected from different regions in a capillary or like sample container. Suitable methods and apparatus are described in U.S. Pat. No. 5,325,170 and WO-A-01/14858, which are hereby incorporated by reference. The reflected or back scattered light is viewed across a range of angles with respect to the laser light path. The reflections generate an interference pattern that moves in relation to such angles upon changing refractive index of the sample. The small angle interference pattern traditionally considered has a repetition frequency in the refractive index space that limits the ability to measure refractive index to refractive index changes causing one such repetition. In one aspect, such refractive index changes are typically on the order of three decades. In another aspect, such changes are on the order of many decades. In another aspect, the fringes can move over many decades up to, for example, the point where the refractive index of the fluid and the channel are matched.

BSI methods direct a coherent light beam along a light path to impinge on a first light transmissive material and pass there through, to pass through a sample which is to be the subject of the measurement, and to impinge on a further light transmissive material, the sample being located between the first and further materials, detecting reflected light over a range of angles with respect to the light path, the reflected light including reflections from interfaces between different substances including interfaces between the first material and the sample and between the sample and the further material which interfere to produce an interference pattern comprising alternating lighter and darker fringes spatially separated according to their angular position with respect to the light path, and conducting an analysis of the interference pattern to determine there from the refractive index, wherein the analysis comprises observation of a parameter of the interference pattern which is quantitatively related to sample refractive index dependent variations in the intensity of reflections of light which has passed through the sample.

The analysis comprises one or both of: (a) the observation of the angle with respect to the light path at which there is an abrupt change in the intensity of the lighter fringes, or (b) the observation of the position of these fringes of a low frequency component of the variation of intensity between the lighter and darker fringes. The first of these (a), relies upon the dependency of the angle at which total internal reflection occurs at an interface between the sample and the further material on the refractive index of the sample. The second (b), relies upon the dependency of the intensity of reflections from that interface on the refractive index as given by the Fresnel coefficients. The rectangular chips also have a single competent from diffraction at the corners.

The first material and the further material are usually composed of the same substance and may be opposite side walls of a container within which the sample is held or conducted. For instance, the sample may be contained in, e.g. flowed through, a capillary dimensioned flow channel such as a capillary tube. The side wall of the capillary tube nearer the light source is then the "first material" and the opposite side wall is the "further material." The cross-sectional depth of the channel is limited only by the coherence length of the light and its breadth is limited only by the width of the light beam. Preferably, the depth of the channel is from 1 to 10 um, but it may be from 1 to 20 um or up to 50 um or more, e.g. up to 1 mm or more. However, sizes of up to 5 mm or 10 mm or more are possible. Suitably, the breadth of the channel is from 0.5 to 2 times its depth, e.g., equal to its depth.

Typically, at least one the interfaces involving the sample at which light is reflected is curved in a plane containing the light path, the curved interface being convex in the direction facing the incoming light if it is the interface between the first material and the sample and being concave in the direction facing the incoming light if it is the interface between the sample and the further material. The sample is typically a liquid, and can be flowing or stationary. However, the sample can also be a solid or a gas in various aspects of the present invention. The first and/or further materials will normally be solid but in principle can be liquid, e.g., can be formed by a sheathing flow of guidance liquid(s) in a microfluidic device, with the sample being a sheathed flow of liquid between such guidance flows. The sample may also be contained in a flow channel of appropriate dimensions in substrate such as a microfluidic chip. The method may therefore be employed to obtain a read out of the result of a reaction conducted on a "lab on a chip" type of device.

In contrast to conventional BSI techniques, the present invention provides systems, apparatuses, and methods for the analysis of non-aqueous samples, solvents, and systems. In one aspect, the ability to analyze non-aqueous systems can provide information on chemical and biological interactions previously only attainable by either destructive or complicated, time consuming methods.

Non-Aqueous Systems

As described above, intermolecular interactions are fundamental in all aspects of chemistry and biochemistry. In organic chemistry, intermolecular interactions have become increasingly more important as scientists explore and optimize synthesis, molecular recognition, and organocatalysis reactions and methods. Thus, the ability to monitor and analyze molecular interaction can be of great use in developing new compositions and methods.

For example, many synthetic reactions utilize substrate-catalyst interactions to drive reactions to completion and obtain enantiomerically enriched products. Traditionally, these interactions have been studied using such methods as isotope incorporation, NMR, UV-Vis spectroscopy, fluorescence, and calorimetry. While these techniques can provide molecular interaction information, they often require high concentrations, large volume samples, and complicated methods.

With respect to organic catalysis, significant research has been expended to design and develop new catalysts and catalyst systems. Accordingly, it would be advantageous to be able to study their interactions without using large quantities of catalyst and potentially expensive substrates. Moreover, some catalyst systems have kinetics that are not suitable for study by techniques such as ITC.

Conventional BSI analysis has been used to study interactions in aqueous solvents. In various aspects, the present disclosure provides systems and methods for analyzing non-aqueous systems, such as, for example, metal-ligand interactions. In an exemplary aspect, the present disclosure provides methods and techniques for analyzing the complexation of tetramethylammonium benzoate (TMAB) with 1,3-diphenyl urea (DPU), 1,3-diphenylthiourea (DPTU), 1,3-bis(pnitrophenyl) urea (DNPU), and 1,3-bis(p-nitrophenyl)thiourea (DNPTU) in acetonitrile (MeCN). In another aspect, BSI can be an efficient method to study small molecule interactions in non-aqueous systems, especially when compared to other free-solution techniques such as calorimetry.

Urea and thiourea have been widely studied in molecular recognition because of their ability to form strong hydrogen bonds. Hydrogen bonding through urea and thiourea derivatives can be used to recognize carboxylic acids, sulfonic acids, and nitrates. Ureas and thioureas can also act as acid catalysts in a variety of organic reactions, such as, for example, Diels-Alder reactions and Claisen rearrangements. In addition, these catalysts are very useful in diastereo- and enantioselective reactions. As a result, the strength of the interaction between a substrate and catalyst can be important information when designing and/or optimizing chemical reactions.

Thus, in various aspects, the inventive BSI techniques can be used to study reactions such as the affinity of benzoates, carboxylates, and other biologically relevant anions or ureas and thioureas in non-aqueous solvents. In another aspect, information gained from BSI analysis on non-aqueous systems can enhance the mechanistic understanding of important biomimetic methods or synthetic chemistries.

The methods and techniques described herein can be performed for any non-aqueous system and/or analyte species. In one aspect, BSI is performed on a non-aqueous system having a solvent comprising acetonitrile. In another aspect, a sample can comprise one or more non-aqueous solvents, such as, for example, a hydrocarbon solvent, provided that such solvent and/or sample is compatible with the materials and devices utilized. In various aspects, a solvent and/or sample can comprise a ketone, aldehyde, alkane, chlorocarbon, sulfoxide, or other solvent, or a combination thereof, and the present invention is not intended to be limited to any particular solvent and/or sample system. In another aspect, any solvent having a refractive index different from that of the chip material can be used. In still another aspect, one or more supercritical fluids can be used as a solvent, provided that the refractive index of the supercritical fluid or mixture is different from that of the chip material. In one aspect, the solvent does not comprise dimethylsulfoxide.

In another aspect, a solvent and/or sample can comprise a mixture of two or more solvents having the same or different polarities. In another aspect, a solvent mixture can be selected based on, for example, Hansen solubility parameters, so as to be compatible with one or more analytes of interest. In yet another aspect, the composition of a solvent can be adjusted during the course of an analysis so as to provide, for example, a gradient.

Channel

The channel of the present invention can, in various aspects, be formed from a substrate such as a piece of silica or other suitable optically transmissive material. In one aspect, the material of composition of the substrate has a different index of refraction than that of the sample to be analyzed. In another aspect, as refractive index can vary significantly with temperature, the substrate can optionally be mounted and/or connected to a temperature control device. In yet another aspect, the substrate can be tilted, for example, about 7°, such that scattered light from channel can be directed to a detector.

In one aspect, the channel has a generally semi-circular cross-sectional shape. A unique multi-pass optical configuration is inherently created by the channel characteristics, and is based on the interaction of the unfocused laser beam and the curved surface of the channel that allows interferometric measurements in small volumes at high sensitivity. Alternatively, the channel can have a substantially circular or generally rectangular cross-sectional shape. In one aspect, the substrate and channel together comprise a capillary tube.

In a further aspect, the substrate and channel together comprise a microfluidic device, for example, a silica substrate, or a polymeric substrate [e.g., polydimethylsiloxane (PDMS) or polymethyl methacrylate (PMMA)], and an etched channel formed in the substrate for reception of a sample, the channel having a cross sectional shape. In one aspect, the cross sectional shape of a channel is semi-circular. In another aspect, the cross sectional shape of a channel is square, rectangular, or elliptical. In other aspects, the cross sectional shape of a channel can comprise any shape suitable for use in a BSI technique. In another aspect, a substrate can comprise one or multiple channels of the same or varying dimensions. In various aspects, the channel can have a radius of from about 5 to about 250 micrometers, for example, about 5, 10, 20, 30, 40, 50, 75, 100, 150, 200, or 250 micrometers. In still other aspects, the channel can have a radius of up to about 1 millimeter or larger, such as, for example, 0.5 millimeters, 0.75 millimeters, 1 millimeter, 1.25 millimeters, 1.5 millimeters, 1.75 millimeters, 2 millimeters, or more.

In one aspect, a microfluidic channel, if present, can hold and/or transport the same or varying samples, and a mixing zone. The design of a mixing zone can allow at least initial mixing of, for example, one or more binding pair species. In another aspect, the at least initially mixed sample can then optionally be subjected to a stop-flow analysis, provided that the reaction and/or interaction between the binding pair species continues or is not complete at the time of analysis. The specific design of a microfluidic channel, mixing zone, and the conditions of mixing can vary, depending on such factors as, for example, the concentration, response, and volume of a sample and/or species, and one of skill in the art, in possession of this disclosure, could readily determine an appropriate design.

In one aspect, a channel comprises a single zone along its length for analysis. In another aspect, a channel can be divided into multiple discrete zones along the length of the channel, such as, for example, 2, 3, 4, 5, 6, 7, 8, 9, 10, or more zones. If a channel is divided into zones, any individual zone can have dimensions, such as, for example, length, the same as or different from any other zones along the same channel. In one aspect, at least two zones have the same length. In another aspect, all of the zones along a channel have the same or substantially the same length. In various aspects, each zone can have a length along the channel of from about 1 to about 1,000 micrometers, for example, about 1, 2, 3, 5, 8, 10, 20, 40, 80, 100, 200, 400, 800, or 1,000 micrometers. In other aspects, each zone can have a length of less than about 1 micrometer or greater than about 1,000 micrometer, and the present disclosure is not intended to be limited to any particular zone dimension. In one aspect, at least one zone can be used as a reference and/or experimental control. In yet another aspect, each measurement zone can be positioned adjacent to a reference zone, such that the channel comprises alternating measurement and reference zones. It should be noted that the zones along a channel do not need to be specifically marked or delineated, only that the system be capable of addressing and detecting scattered light from each zone.

In another aspect, any one or more zones in a channel can be separated from any other zones by a junction, such as, for example, a union, coupling, tee, injection port, mixing port, or a combination thereof. For example, one or more zones in the flow path of a sample can be positioned upstream of an injection port where, for example, an analyte can be introduced. In such an aspect, one or more zones can also be positioned downstream of the injection port.

In yet another aspect, a channel can be divided into two, three, or more regions, wherein each region is separated from other regions by a separator. In one aspect, a separator can prevent a fluid in one region of a channel from contacting and/or mixing with a fluid from another region of the channel. In another aspect, any combination of regions or all of the regions can be positioned such that they will be impinged with at least a portion of the light beam. In such an aspect, multiple regions of a single channel can be used to conduct multiple analyses of the same of different type in a single instrumental setup. In one aspect, a channel has two regions, wherein a separator is positioned in the channel between the two regions, and wherein each of the regions are at least partially in an area of the channel where the light beam is incident.

In one aspect, if multiple regions are present, each region can have an input and an output port. In one aspect, the input and/or output ports can be configured so as not to interfere with the generation of scattered light, such as, for example, backscattered light, and the resulting measurements. It should be noted that other geometric designs and configurations can be utilized, and the present invention is not intended to be limited to the specific exemplary configurations disclosed herein. Thus, in one aspect, a single channel can allow for analysis of multiple samples simultaneously in the same physical environment.

In one aspect, a separator, if present, comprises a material that does not adversely affect detection in each of the separated regions, such as, for example, by creating spurious light reflections and refractions. In one aspect, a separator is optically transparent. In another aspect, a separator does not reflect light from the light source. In such an aspect, a separator can have a flat black, non-reflective surface. In yet another aspect, the separator can have the same or substantially the same index of refraction as the channel. In yet another aspect, a separator can be thin, such as, for example, less than about 2 µm, less than about 1 µm, less than about 0.75 µm.

Any one or more individual zones along a channel, or any portion of a channel can optionally comprise a marker compound positioned within the path of the channel. In one aspect, a marker compound can be positioned on the interior surface of a capillary such that a sample, when introduced into the channel, can contact and/or interact with the marker compound.

A marker compound, if present, can comprise any compound capable of reacting or interacting with a sample or an analyte species of interest. In one aspect, a marker compound can comprise a chromophore. In another aspect, a marker compound can comprise a ligand that can interact with a species of interest to provide a detectable change in refractive index.

Light Source

In one aspect, the light source generates an easy to align optical beam that is incident on the etched channel for generating scattered light. In another aspect, the light source generates an optical beam that is collimated, such as, for example, the light emitted from a HeNe laser. In another aspect, the light source generates an optical beam that is not well collimated and disperses in, for example, a Gaussian profile, such as that generated by a diode laser. In another aspect, at least a portion of the light beam is incident on the channel such that the intensity of the light on any one or more zones is the same or substantially the same. In another aspect, the portion of the light beam incident on the channel can have a non-Gaussian profile, such as, for example, a plateau (e.g., top-hat). The portion of the light beam in the wings of the Gaussian intensity profile can be incident upon other portions of the channel or can be directed elsewhere. In one aspect, variations in light intensity across the channel can result in measurement errors. In still another aspect, if portions of a light beam having varying intensity are incident upon multiple zones or portions of a channel, a calibration can be performed wherein the expected intensity of light, resulting interaction, and scattering is determined for correlation of future measurements.

The light source can comprise any suitable equipment and/or means for generating light, provided that the frequency and intensity of the generated light are sufficient to interact with a sample and/or a marker compound and provide elongated fringe patterns as described herein. Light sources, such as HeNe lasers and diode lasers, are commercially available and one of skill in the art could readily select an appropriate light source for use with the systems and methods of the present invention. In one aspect, a light source can comprise a single laser. In another aspect, a light source can comprise two or more lasers, each generating a beam that can impinge one or more zones of a channel. In another aspect, if two or more lasers are present, any individual laser can be the same as or different from any other laser. For example, two individual lasers can be utilized, each producing a light beam having different properties, such as, for example, wavelength, such that different interactions can be determined in each zone along a channel.

As with any interferometric technique for micro-chemical analysis, it can be advantageous, in various aspects, for the light source to have monochromaticity and a high photon flux. If warranted, the intensity of a light source, such as a laser, can be reduced using neutral density filters.

The systems and methods of the present invention can optionally comprise an optical element that can focus, disperse, split, and/or raster a light beam. In one aspect, an optical element, if present, can at least partially focus a light beam onto a portion of the channel. In various aspects, such an optical element can facilitate contact of the light beam with one ore more zones along a channel. In one aspect, a light source, such as a diode laser, generates a light beam having a Gaussian profile, and an optical element is not necessary or present. In another aspect, a light source, such as a diode laser, can be used together with an optical focusing element. In another aspect, a light source, such as a HeNe laser, generates a collimated light beam and an optical element can be present to spread the light beam and facilitate contact of the light beam with at least two zones along the channel. Such a light beam configuration can allow for multiple measurements or sample and reference measurements to be made simultaneously or substantially simultaneously within the same channel.

In various aspects, an optical element, if present, can comprise a dispersing element, such as a cylindrical lens, capable of dispersing the light beam in at least one direction; a beam splitting element capable of splitting a well collimated light beam into two or more individual beams, each of which can be incident upon a separate zone on the same channel; a rastering element capable of rastering a light beam across one or more zones of a channel; or a combination thereof.

In yet other aspects, one or more additional optical components can be present, such as, for example, a minor, a neutral density filter, or a combination thereof, so as to direct the light beam and/or the scattered light in a desired direction or to adjust one or more properties of a light beam.

Impingement

At the channel, the light beam should have a profile such that the light beam impinges the channel in the area of interest. In one aspect, the light beam impinges the channel over a single zone or portion of the channel. In another aspect, the light beam impinges the channel over multiple, for example, 2, 3, 4, or more zones. In one aspect, the intensity of the light beam is uniform or substantially uniform across each of the discrete zones of interest along the channel. In another aspect, the light beam is dimensioned so as to fill or slightly overfill the channel or at least that portion of the channel to be interrogated. In another aspect, the light beam is aligned such that it impinges the channel perpendicular to the central axis of the channel. In yet another aspect, the width of the light beam is parallel to the longitudinal axis of the channel.

In another aspect, the alignment of the light beam exhibits no or substantially no tilt or skew with respect to the channel. In one aspect, the alignment of the light beam and the capillary can be such that the resulting fringe patterns are positioned above or below the incoming beam. In one aspect, misalignment or poor alignment of the light beam with the channel can result in distorted and/or skewed interference fringes due to the uneven distribution of light beam energy at the point of impingement with the channel.

Other than alignment of the light beam with respect to the channel, the position and orientation of the light source, optional optical element, channel, and detector, can vary according to a particular experimental design, provided that scattered light can be generated by reflective and refractive interactions of the light beam with the substrate/channel interface, sample, and optional marker compounds. One of skill in the art in possession of this disclosure could readily determine an appropriate arrangement of the light source, optional optical element, channel, and detector.

When incident upon a channel having a sample therein, and optionally one or more marker compounds positioned in zones along the channel, the incident light can scatter and comprise elongated interference fringes due to reflective and refractive interaction with the sample, channel walls, and marker compounds, if present. These elongated fringe patterns can comprise a plurality of light bands whose positions shift as the refractive index of the sample is varied, either through compositional changes or through temperature changes, for example. In one aspect, the scattered light comprises backscattered light. In another aspect, the optical elements and channel can be positioned so as to result in side scattering of the light beam. In yet another aspect, the optical elements and channel can be positioned to measure light passed through a channel, such as, for example, when using a fluorescent analyte or probe species, or an absorbing species.

Detector

A detector detects the scattered light and converts it into intensity signals that vary as the positions of the light bands in the elongated fringe patterns shift, and can thus be employed to determine the refractive index (RI), or an RI related characteristic property, of the sample. Exemplary properties that can be detected and/or quantified using the inventive techniques can comprise, without limitation, changes in conformation, structure, charge level, level of hydration, or a combination thereof. In other aspects, the progress of one or more chemical reactions can be monitored, such as, for example, that can occur in an aqueous or a non-aqueous solvent.

The detector can, in various aspects, comprise any suitable image sensing device, such as, for example, a bi-cell sensor, a linear or area array CCD or CMOS camera and laser beam analyzer assembly, a photodetector assembly, an avalanche photodiode, or other suitable photodetection device. In one aspect, the detector is a photodetector. In another aspect, the detector is an array photodetector capable of detecting multiple interference fringe patterns. In yet another aspect, a detector can comprise multiple individual detectors to detect interference fringe patterns produced by the interaction of the light beam with the sample, channel wall, and optional marker compounds. In one aspect, the scattered light incident upon the detector comprises interference fringe patterns. In another aspect, the scattered light incident upon the detector comprises elongated interference fringe patterns that correspond to the discrete zones along the length of the channel. The specific position of the detector can vary depending upon the arrangement of other elements. In one aspect, the detector can be positioned at an approximately 45° angle to the channel.

The intensity signals from the detector can then be directed to a signal analyzer for fringe pattern analysis and determination of the RI or RI related characteristic property of the sample and/or reference in each zone of the channel. The signal analyzer can be a computer or a dedicated electrical circuit. In one aspect, the signal analyzer includes the programming or circuitry necessary to determine from the intensity signals, the RI or other characteristic property of the sample in each discrete zone of interest. In another aspect, the signal analyzer is capable of detecting positional shifts in interference fringe patterns and correlating those positional shifts with a change in the refractive index of at least a portion of the sample. In another aspect, the signal analyzer is capable of detecting positional shifts in interference fringe patterns and correlating those positional shifts with a change in the refractive index occurring in a portion of the channel. In yet another aspect, the signal analyzer is capable of comparing data received from a detector and determining the refractive index and/or a characteristic property of the sample in any zone or portion of the channel.

In other aspects, the signal analyzer is capable of interpreting an intensity signal received from a detector and determining one or more characteristic properties of the sample. In still other aspects, the signal analyzer can utilize a mathematical algorithm to interpret positional shifts in the interference fringe patterns incident on a detector. In another aspect, known mathematical algorithms and/or signal analysis software, such as, for example, deconvolution algorithms, can be utilized to interpret positional shifts occurring from a multiplexed scattering interferometric analysis.

The detector can be employed for any application that requires interferometric measurements; however, the detector can be particularly useful for making universal solute quantification, temperature and flow rate measurements. In these applications, the detector provides ultra-high sensitivity due to the multi-pass optical configuration of the channel. In the temperature measuring aspect, a signal analyzer receives the signals generated by the photodetector and analyzes them using the principle that the refractive index of the sample varies proportionally to its temperature. In this manner, the signal analyzer can calculate temperature changes in the sample from positional shifts in the detected interference fringe patterns. In one aspect, the ability to detect interference fringe patterns from interactions occurring along a channel can provide real-time reference and/or comparative measurements without the problem of changing conditions between measurements. In one aspect, a signal analyzer, such as a computer or an electrical circuit, can thus be employed to analyze the photodetector signals, and determine the characteristic property of the sample.

In the flow measuring aspect, the same principle is also employed by the signal analyzer to identify a point in time at which perturbation is detected in a flow stream in the channel. In the case of a thermal perturbation, a flow stream whose flow rate is to be determined, is locally heated at a point that is known distance along the channel from the detection zone. The signal analyzer for this aspect includes a timing means or circuit that notes the time at which the flow stream heating occurs. Then, the signal analyzer determines from the positional shifts of the light bands in the interference fringe patterns, the time at which thermal perturbation in the flow stream arrives at the detection zone. The signal analyzer can then determine the flow rate from the time interval and distance values. Other perturbations to the flow stream, include, but are not limited to, introduction into the stream of small physical objects, such as glass microbeads or nanoparticles. Heating of gold particles in response to a chemical reaction or by the change in absorption of light due to surface-bound solutes or the capture of targets contained within the solution can be used to enhance the temperature induced RI perturbation and thus to interrogate the composition of the sample. In another aspect, measurements at multiple zones along the channel can be used to determine temperature gradients or rate of temperature change of a sample within the channel.

In one aspect, the systems and methods of the present invention can be used to obtain multiple measurements simultaneously or substantially simultaneously from discrete zones along the length of a channel. In such an aspect, each zone can provide a unique measurement and/or reference. For example, a series of reactive species can be used as marker compounds, positioned in zones along the channel, each separated by a reference zone. In another aspect, temporal detection can be used to measure changes in a sample over time as the sample flows through the channel, for example, with a flow injection analysis system.

In another aspect, two or more samples, blanks, and/or references can be positioned in the channel such that they are separated by, for example, an air bubble. In another aspect, each of a plurality of samples and/or reference species can exhibit a polarity and/or refractive index the same as or different from any other samples and/or reference species. In one aspect, a pipette can be used to place a portion of a reference compound into the channel. Upon removal of the pipette, an air bubble can be inserted between the portion of the reference compound in the channel and a portion of a sample compound, thereby separating the reference and sample compounds and allowing for detection of each in a flowing stream within the channel. In another aspect, each sample and/or reference compound can be separated by a substance other than air, such as, for example, water, oil, or other solvent having a polarity such that the sample and/or reference compounds are not miscible therewith.

In one aspect, the sample is a fluid. In another aspect, the sample is a liquid, which can be a substantially pure liquid, a solution, or a mixture. In a further aspect, the sample can further comprise one or more analytes. In one aspect, a sample can be introduced into the channel via an injection port at, for example, one end of the channel.

As the light beam impinges one or more discrete regions of a channel, the resulting interference fringe patterns can move with a change in refractive index. The ability to analyze multiple discrete zones simultaneously can provide high spatial resolution and can provide measurement techniques with an integrated reference.

Interferometric Detection System

In one aspect, the invention relates to an interferometric detection system and method that can be used, for example, for detection of refractive index changes in picoliter sized volumes for chip-scale analyses. Conventional backscattering interferometry, as illustrated in FIG. 1, utilizes interference fringes generated by backscattered light to detect refractive index changes in a sample. The backscatter detection technique is generally disclosed in U.S. Pat. No. 5,325,170 to Bornhop, and U.S. Patent Publication No. US2009/0103091 to Bornhop, both of which are hereby incorporated by reference. With reference to FIG. 1, a conventional backscattering interferometric detection system 10 comprises a laser 12 that produces a light beam 14. The light beam can be directed through one or more neutral density filters 16 to reduce the intensity of the light beam, before being reflected on a mirror 18 and directed to impinge an etched channel 22 on a chip 20. The chip can also be positioned on a temperature controlled support block 23 and/or an X-Y translation stage 24. After various reflective and refractive interactions with the channel and sample, the scattered light can be directed to a detector 25, and the intensity signals generated by the detector interpreted by a computer based signal analyzer 28.

In another aspect, the inventive interferometric detection system and methods are capable of measuring multiple signals, for example, along a length of a capillary channel, simultaneously or substantially simultaneously. In one aspect and while not wishing to be bound by theory, the refractive index changes that can be measured by the multiplexed interferometric detection systems and methods of the present disclosure can arise from molecular dipole alterations associated with conformational changes of sample-ligand interaction as well as density fluctuations.

The detection system has numerous applications, including the observation and quantification of molecular interactions, molecular concentrations, ligand-metal interactions, non-aqueous electrochemical reactions, ultra micro calorimetry, flow rate sensing, and temperature sensing.

In one aspect, the detection systems and methods described herein can be useful as a bench-top molecular interaction photometer. In another aspect, the detection systems and methods described herein can be useful for performing bench-top or on-site analysis.

In another aspect, the interferometric detection system comprises a substrate, a channel formed in the substrate for reception of a sample to be analyzed, a light source for generating a light beam, directing the light beam onto the substrate such that the light beam is incident on at least a portion of the channel and thereby generate scattered light through reflective and refractive interaction of the light beam with a substrate/channel interface and the sample, the scattered light comprising interference fringe patterns, a photodetector for receiving scattered light from each of the two or more discrete zones and generating a plurality of intensity signals, and at least one signal analyzer for receiving the intensity signals and determining therefrom one or more characteristic properties of the sample along the length of the channel.

Interferometric Detection Methods

In one aspect, the present invention provides a method for determining a characteristic property of a non-aqueous sample comprising the steps of providing an apparatus adapted for performing light scattering interferometry, the apparatus comprising a substrate, a channel formed in the substrate capable of receiving a sample to be analyzed, a light source for generating a light beam, a photodetector for receiving scattered light and generating a plurality of intensity signals, and at least one signal analyzer capable of receiving the intensity signals and determining therefrom one or more characteristic properties of the sample, and interrogating the sample using light scattering interferometry.

Analysis of Non-Aqueous Systems

In one aspect, the present disclosure provides analysis methods for monitoring molecular interactions involving an organic and/or non-aqueous species. In another aspect, the present disclosure provides backscattering interferometric (BSI) analysis methods that can be used, for example, to probe binding affinity between benzoate and derivates of urea and thiourea.

As in conventional BSI, the inventive methods, in one aspect, monitor a change in refractive index to determine the binding affinity of molecular interactions. In such an aspect, the introduction of two binding partners into the channel can create a change in refractive index, resulting in a spatial shift in the generated fringe pattern. In one aspect, the magnitude of this shift depends on the precise fringes interrogated, the concentration of the binding pairs, conformational changes initiated upon binding, changes in water of hydration, and binding affinity.

Urea and thiourea have been widely studied in molecular recognition because of their ability to form strong hydrogen bonds. Hydrogen bonding through urea and thiourea derivatives are used to recognize carboxylic acids, sulfonic acids, and nitrates. Ureas and thioureas also act as acid catalysts in a variety of organic reactions including the Diels-Alder reaction and Claisen rearrangement. In addition, these catalysts are very useful in diastereo- and enantioselective reactions. Thus, molecular interaction information for these species can be beneficial for understanding and designing, for example, chemical processes.

In another aspect, it should be noted that, when used on non-aqueous samples, BSI techniques can detect specific binding interactions, as opposed to merely detecting non-specific interactions. In one aspect, the non-aqueous BSI techniques described herein can be useful in monitoring interactions not otherwise detectable using conventional BSI techniques. In various aspects, the non-aqueous BSI techniques can be useful in monitoring, for example, small molecule hydrogen bonding interactions, molecular recognition experiments, and/or organocatalysts.

The present study demonstrates the applicability of BSI as a tool for studying small molecule interaction in non-aqueous solvents. Not only is BSI able to recognize the formation of just two hydrogen bonds, but it can also distinguish between TMAB complexation with DPU/DPTU and DNPU/DNPTU with an affinity difference of more than one order of magnitude. BSI experiments have the advantage of using smaller volumes and lower concentrations than ITC and ellipsometry. The microfluidic channel used in these BSI experiments has a cross-sectional area of 2.9 nm2 that, when interrogated by a 100 μm diameter laser, provides an optical probe volume of ca. 290 μL. Therefore at the lowest concentrations used in these experiments, BSI can detect an interaction between ca. 261.9 million molecules.

When compared to the concentrations and volumes used for ITC and ellipsometry, BSI is 6 orders of magnitude more sensitive than ITC and 8 orders of magnitude more than ellipsometry. This makes BSI interaction-efficient, with the ability to detect a relatively small number of discreet interactions when compared to other free-solution techniques.

The simple, user-friendly design of BSI provides a technique by which organic chemists can screen for molecules by following a change in refractive index.

In one aspect, non-aqueous BSI techniques can facilitate the analysis of systems that have, for example, poor aqueous phase solubility, for example, with small molecule pharmaceutical candidates. While not wishing to be bound by theory, it is expected that any small changes in the solvent or sample matrix, such as the addition of DMSO to a solvent system, can produce a background signal. Thus, in one aspect, the addition of an amount of a solvent, such as, for example, DMSO, can enable molecular interaction studies in antibody-antigen interactions in non-aqueous media.

Detection of Chemical Events

The disclosed systems and methods can be used in connection with the detection and determination of a wide variety of characteristic properties of a sample. For example, the invention can be used to determine absolute or relative refractive index (RI) of a sample, for example a fluid either flowing or static. The disclosed systems and methods can also be used in connection with detection and determination of chemical events, for example the formation of hydrogen bonds in an organic reaction.

In one aspect, the disclosed systems and methods can be used in connection with a step of performing a chromatographic separation or a separation of the sample prior to the determining the characteristic property step.

Analytical Detection Events

In one aspect, the invention also finds use as a detector for other chip-scale analytical schemes including chromatographic separations and FIA. In another aspect, it is possible to detect catalyst species and their interaction with chemical reactants. In another aspect, the interferometric techniques can be used to quantify environmental analytes. In yet another aspect, micro-thermometry can be performed, wherein the device has the capability of measuring small temperature changes (in the $10^{-3\circ}$ C. range) allowing for calorimetry and fundamental chemical binding studies to be performed in picoliter volumes.

Measurement of End-Point Values

In one aspect, multiplexed BSI can measure end-point values of phase for the reaction between molecule A and molecule B as a function of the concentration of molecule B to determine the binding affinity of the complex and/or to quantitatively determine the concentration of the A-B product at reaction equilibrium. End-point concentration bioassays can be used in both research and clinical diagnostic applications.

Determination of Kinetic Parameters

In a further aspect, BSI can determine kinetic parameters. That is, the interferometric detection technique described herein can be used to monitor various kinetic parameters, such as, for example, binding affinities, of a chemical and/or biochemical analyte species. The use of BSI for the determination of a kinetic parameter can provide one or more advantages over traditional techniques, for example, free-solution measurements of label-free species, high throughput, small sample volume, high sensitivity, and broad dynamic range. A BSI technique can be performed on a free-solution species, a surface immobilized species, or a combination thereof. In one aspect, the species of interest is a free-solution species, wherein at least a portion of the species of interest is not bound or otherwise immobilized. In another aspect, at least a portion of the species of interest is surface immobilized.

In one aspect, a BSI technique can be used to analyze and/or quantify one or more molecular interactions, such as, for example, a dissociation constant for one or more binding pair species.

The sensitivity of a multiplexed BSI technique can allow analysis and/or determination of at least one kinetic parameter to be performed on a small volume sample. The volume of a sample comprising at least one species of interest can, in various aspects, be less than about 1 nL, for example, about 900, 850, 800, 700, 600, 500, 400, 350, 300, 250, or 200 pL; less than about 600 pL, for example, about 580, 550, 500, 450, 400, 350, 300, 250, or 200 pL; or less than about 400 pL, for example, about 390, 380, 370, 360, 350, 340, 330, 320, 310, 300, 280, 250, 230, or 200 pL. In one aspect, the sample volume is about 500 pL. In another aspect, the sample volume is about 350 pL. The sample volume can also be greater than or less than the volumes described above, depending on the concentration of a species of interest and the design of a particular BSI apparatus. A species that can be analyzed via BSI can be present in neat form, in diluted form, such as, for example, in a dilute solution, or any other form suitable for analysis by a BSI technique. The concentration of a species of interest can likewise vary depending upon, for example, the design of a particular BSI apparatus, the volume of sample in the optical path, the intensity of a response of a specific species to the radiation used in the experiment. In various aspects, the species can be present at a concentration of from about 1 pM to greater than 100 mM.

Analysis of a kinetic parameter via a BSI technique can be performed on a static sample, a flowing sample, for example, 75-120 µL/min, or a combination thereof. In another aspect, analysis of a kinetic parameter via a BSI technique can be performed on a flowing sample having a flow rate of, for example, 10-1,000 nl/min, or less. In one aspect, an analysis can be a stop-flow determination that can allow an estimation of the dissociation constant ($K_D$) of one or more binding pairs of species. The speed at which one or more samples can be analyzed can be dependent upon, inter alia, the data acquisition and/or processing speed of the detector element and/or processing electronics.

The concentration of one or more analyte species in a sample can be determined with a BSI technique by, for example, monitoring the refractive index of a sample solution comprising an analyte species. A property, such as, for example, refractive index, can be measured in real-time and the kinetics of an interaction between analyte species determined therefrom. Other experimental conditions, such as, for example, temperature and pH, can optionally be controlled during analysis. The number of real-time data points acquired for determination of a kinetic parameter can vary based on, for example, the acquisition rate and the desired precision of a resulting kinetic parameter. The length of time of a specific experiment should be sufficient to allow acquisition of at least the minimal number of data points to calculate and/or determine a kinetic parameter. In one aspect, an experiment can be performed in about 60 seconds.

An apparent binding affinity between binding pair species can subsequently be extracted from the acquired data using conventional kinetics models and/or calculations. In one aspect, a model assumes first order kinetics (a single mode binding) and the observed rate ($k_{obs}$) can be plotted versus the concentration of one of the species. A desired kinetic parameter, such as, for example, $K_D$, can be determined by, for example, a least squares analysis of the relationship plotted above. A suitable fitting model can be selected based on the particular experimental condition such that a rate approximation can be determined at the end of the analysis. One of skill in the art can readily select an appropriate model or calculation to determine a particular kinetic parameter from data obtained via BSI analysis.

In one aspect, BSI can be utilized to measure a free-solution molecular interaction. In another aspect, BSI can be used to measure both a free solution property and a immobilized interaction within the same channel. In a further aspect, BSI can measure label-free molecular interactions.

BSI can be used in any market where measuring macromolecular interactions is desired. In one aspect, a BSI technique, as described herein can be combined with various electrochemical studies. In the food industry, as well as in biodefense applications, a rapid methodology that can assay for the presence of toxins, xenobiotics, allergens, additives, or biowarfare agents whether chemicals, viruses, or cellular pathogens such as certain bacteria can be useful as evidenced by a large number of such items for which no easy to use tests are readily available today. Prior conventional BSI methods were limited to aqueous samples and thus, not amenable to analysis of hydrophobic or other non-aqueous samples.

In summary, BSI can be useful as a tool for studying small molecule interaction in non-aqueous solvents. Non-aqueous BSI techniques are capable of recognizing such changes as the formation of hydrogen bonds, together with being capable of distinguishing between TMAB complexation with DPU/DPTU and DNPU/DNPTU with an affinity difference of more than one order of magnitude. In one aspect, BSI experiments have the advantage of using smaller volumes and lower concentrations than comparable ITC and ellipsometry techniques. In one aspect, when compared to the concentrations and volumes used for ITC and ellipsometry, BSI is, for example, 6 orders of magnitude more sensitive than ITC and 8 orders of magnitude more than ellipsometry. Thus, BSI can be interaction-efficient, with the ability to detect a relatively small number of discreet interactions when compared to other free-solution techniques. The simple, user-friendly design of BSI provides a technique by which organic chemists can screen for molecules by following a change in refractive index.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

In a first example, the complexation of tetramethylammonium benzoate (TMAB) with 1,3-diphenyl urea (DPU), 1,3-diphenylthiourea (DPTU), 1,3-bis(pnitrophenyl) urea (DNPU), and 1,3-bis(p-nitrophenyl)thiourea (DNPTU) in acetonitrile (MeCN) was studied.

End-point experiments of TMAB interaction with DPU and DPTU in MeCN were preformed with BSI. Experiments were carried out in the low to mid micromolar range. For these experiments PU and DPTU concentrations were held constant at 10 µM while TMAB concentration was varied from 5-60 µM. BSI experiments were carried out in a steady-state manner, wherein samples were mixed and allowed to equilibrate for several hours before analysis.

Prior to conducting the BSI experiments, the laser and temperature controller were warmed up for about an hour, and the instrument was aligned with respect to the microfluidic channel and the detector to obtain a single frequency Fourier transform.

Figure 2:
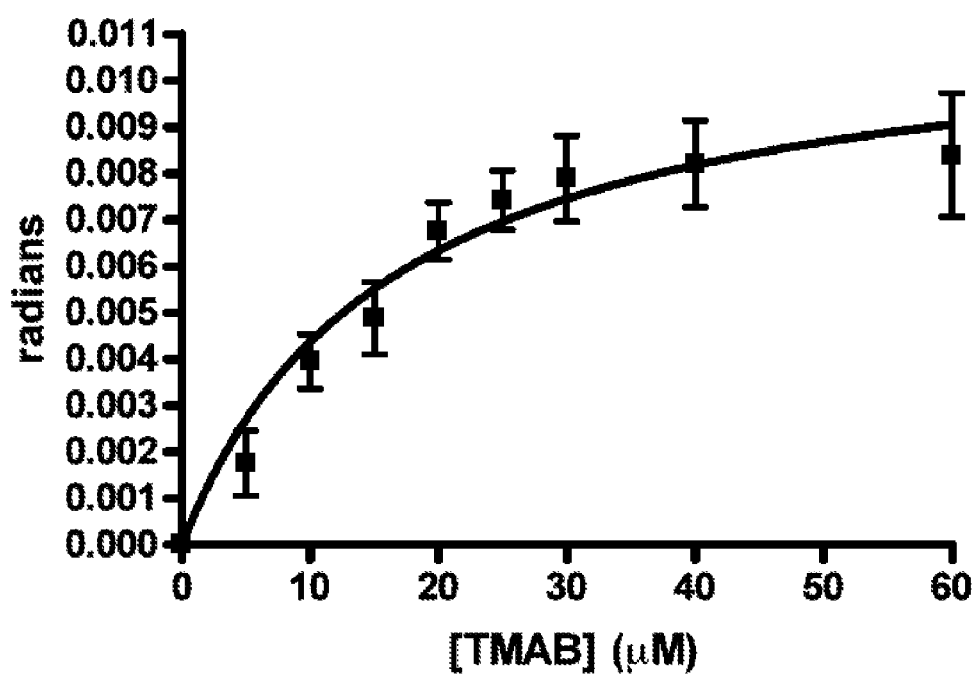
FIG. 2 illustrates steady-state data of 10 μm 1,3-diphenyl urea (DPU) complexed to tetramethylammonium benzoate (TMAB) ranging from 0-60 μM in acetonitrile (MeCN) (curve fitting to a one-site binding hyperbola yielded a $K_D$ of 18.56±4.47 μM with an $R^2$ of 0.97).

The samples were analyzed by pipetting 1 μL of each concentration directly into the channel well and recording the signal for 45 seconds. The zero point of DPU/DPTU only and the TMAB-only calibration curve were subtracted from the binding data to obtain the final binding curve. FIG. 2 illustrates the representative BSI plot and curve-fit of DPU complexation with TMAB. The BSI signal levels out at the high concentration of TMAB, showing a saturation binding curve that can be fit to a one-site binding hyperbola to obtain $K_D$ values. Both DPU and DPTU have similar affinity for TMAB with $K_D$ values of 18.5 and 23.2 μM, respectively (Table 1).

slightly higher affinity for TMAB than DPTU, with respective dissociative binding constants of 21.7 and 27.4 μM. The opposite trend was seen for TMAB interaction with DNPU and DNPTU, with DNPTU having a slightly lower $K_D$ of 1.2 μM and DNPU with a $K_D$ of 1.4 μM. The BSI $K_D$ values are all within experimental error of the ITC data and exhibit the same trends.

In another example, ellipsometry experiments were carried out for the DPU-TMAB interaction to relate the BSI signal shift to changes in refractive index. These experiments were run using a 60° liquid prism cell, measuring the refractive index at 633 nm, the same wavelength used in the BSI experiments. In order to obtain significant changes in the refractive index, the concentrations of the binding pairs were increased, with DPU held constant at 25 μM and TMAB varied from 25-200 μM. The final binding data was obtained by subtracting out the zero point of 25 μM DPU

TABLE 1

BSI and ITC Experiments: $K_D$ values and Thermodynamic data

| TMAB Complexation | BSI $K_D$ (μM) | ITC $K_D$ (μM) | n | ΔH (cal/mol) | ΔS (cal/mol K) |
|---|---|---|---|---|---|
| DPU | 18.56 ± 4.46 | 21.75 ± 12.09 | 0.91 ± 0.04 | −5983.5 ± 1284.2 | 1.5 ± 4.6 |
| DPTU | 23.20 ± 4.55 | 27.43 ± 6.40 | 0.96 ± 0.05 | −6559 ± 384 | −1.1 ± 1.48 |
| DNPU | 0.54 ± 0.08 | 1.35 ± 0.29 | 0.95 ± 0.15 | −6186.1 ± 930.0 | 6.1 ± 3.0 |
| DNPTU | 0.42 ± 0.08 | 1.17 ± 0.29 | 0.97 ± 0.04 | −2464.6 ± 517.6 | 18.9 ± 1.9 |

In a second example, a higher affinity interaction was examined to test the upper limits of BSI as an analytical tool for small molecule interactions. Experiments were carried out on a similar system with TMAB but the DPU and DPTU were modified to include para-substituted nitro groups on both phenyl rings. The nitro groups in DNPU and DNPTU pull electron density away from the urea and thiourea hydrogens, which increases the hydrogen bonding affinity for the benzoate oxygens. These substrates were expected to have higher affinity than the system studied above in the first example. The BSI experiments in this example were carried out at lower concentrations with DNPU/DNPTU concentration held constant at 1 μM and TMAB concentration varied from 0.5-10 μM.

Final binding curves were obtained after subtracting out the TMAB-only data. The binding affinity for both DNPU and DNPTU were similar (Table 1) with $K_D$ values of 0.54 and 0.42 μM, respectively. As expected, the data obtained illustrated the enhanced binding of DNPU and DNPTU to TMAB due to the presence of the p-$NO_2$ groups. The data in Table 1 and subsequent binding curves illustrate similar radian shifts and binding saturation with $R^2$ values of 0.97 or higher.

In a third example, isothermal titration calorimetry (ITC) experiments were performed to benchmark the non-aqueous BSI technique. Initial experiments were carried out with 5 mM TMAB titrated into a sample cell containing 0.5 mM DPU or DPTU in MeCN at 25° C. Next, the interaction of TMAB with either DNPU or DNPTU was investigated using ITC. As with the BSI studies, the ITC experiments were run at slightly lower concentrations than the TMAB-DPU/DPTU ITC experiments, with 2 mM TMAB titrated into 0.2 mM of either DNPU or DNPTU. The results from these experiments are shown in Table 1, with DPU having a from the binding data and then subtracting out the subsequent refractive index calibration curve of the varying concentration of TMAB.

Figure 3:
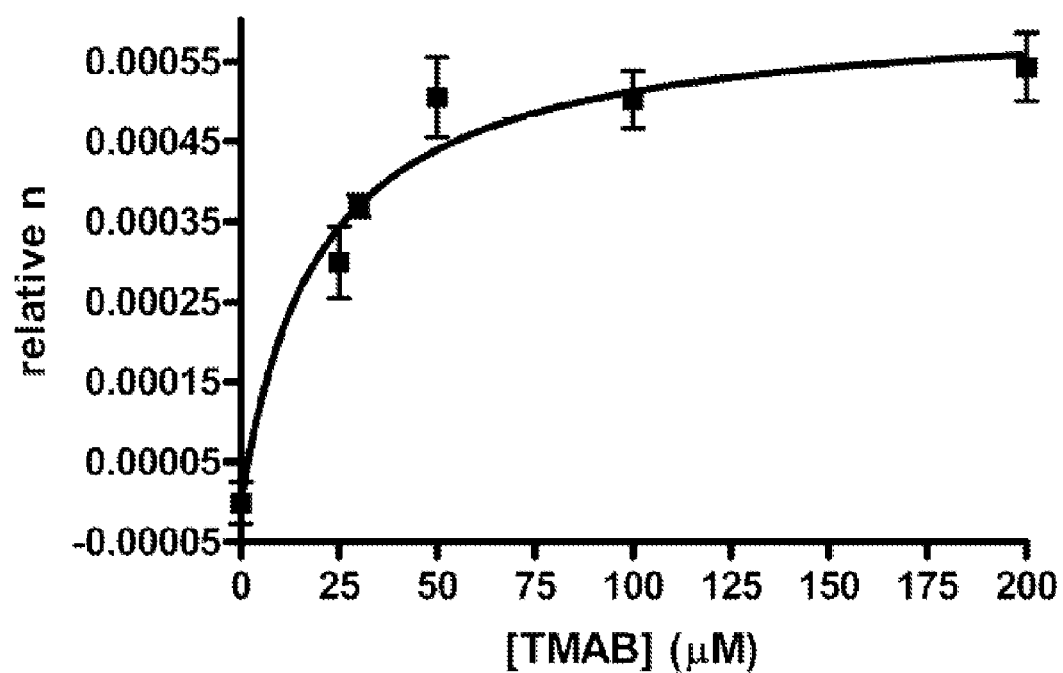
FIG. 3 is a plot of ellipsometry refractive index measurements at 633 nm. The relative refractive index of equilibrated samples containing 25 μM DPU and 0-200 μM TMAB show a saturation binding curve (curve fitting to a one-site binding hyperbola yielded a $K_D$ of 19.40±6.23 μM with an $R^2$ of 0.97).

Analysis of the ellipsometry data was analogous to BSI since the experiments were performed at steady-state and measured the change in refractive index. FIG. 3 illustrates the ellipsometry average plot with the curve fit obtaining a $K_D$ value of 19.40±6.23 μM. The ellipsometry data correlated with the BSI $K_D$ values, providing further evidence that the BSI signal shift is related to variations in refractive index during complex formation.

Figure 4:
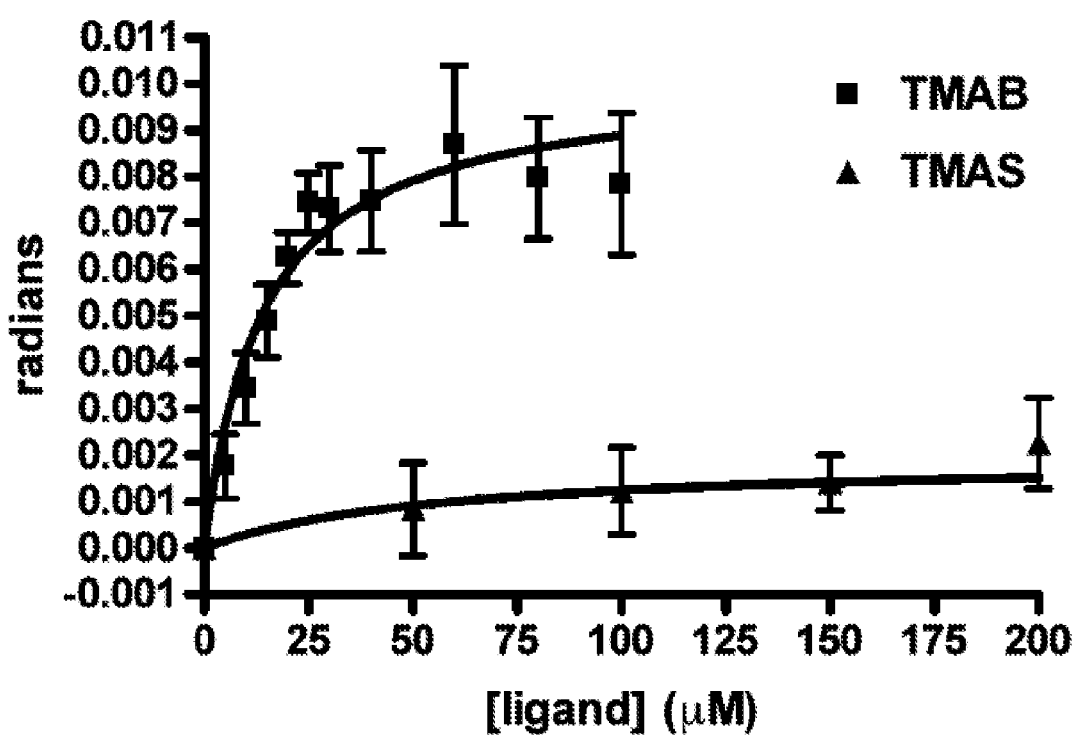
FIG. 4 illustrates steady-state backscattering interferometric data of DPU complexed to TMAB and tetramethylammonium p-toluene sulfonate (TMAS). The large signal shift for TMAB compared to TMAS illustrates that BSI detects specific binding and not a non-specific interaction.

It is also important to note that BSI detects specific binding interactions and does not simply detect non-specific interactions. In order to compare specific versus non-specific binding, experiments were run with DPU and tetramethylammonium sulfonate (TMAS). TMAS is not expected to have a strong affinity for DPU because the sulfonate oxygens are much less electronegative especially in comparison to the benzoate oxygens. FIG. 4 illustrates the negligible signal shift due to DPU-TMAS complexation even at high concentrations whereas DPU-TMAB generates a large signal shift that saturates at much lower concentrations.

Thus, BSI can recognize the formation of just two hydrogen bonds, and can distinguish between TMAB complexation with DPU/DPTU and DNPU/DNPTU with an affinity difference of more than one order of magnitude. BSI experiments have the advantage of using smaller volumes and lower concentrations than ITC and ellipsometry. The microfluidic channel used in these BSI experiments has a cross-sectional area of 2.9 nm2 that, when interrogated by a 100 μm diameter laser, provides an optical probe volume of ca. 290 μL. Therefore at the lowest concentrations used in these experiments, BSI can detect an interaction between ca. 261.9 million molecules.

Figure 5A:
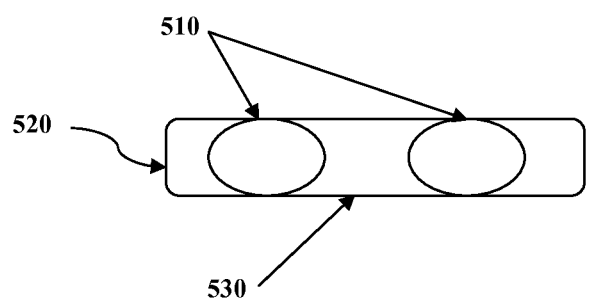
FIG. 5A illustrates an exemplary aspect wherein two or more samples, blanks, and/or references can be positioned in the channel such that they are separated by, for example, an air bubble.
Figure 5B:
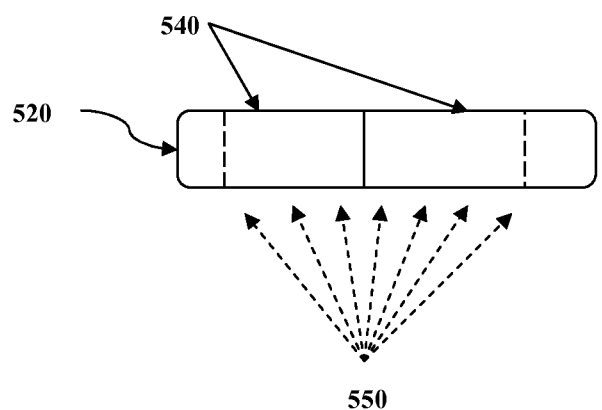
FIG. 5B illustrates an exemplary aspect wherein interrogation occurs at two discrete locations along the channel simultaneously.

In other aspects, as illustrated in FIGS. 5A and 5B, two or more samples 510, blanks, and/or references can be positioned in the channel 520 such that they are separated by, for example, an air bubble 530. In still other aspects, two discrete regions 540 along a channel 520 can be interrogated simultaneously, such that light 550 impinges each of the discrete regions 540.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining a characteristic property of a liquid sample comprising the steps of:
   a. providing an apparatus adapted for performing light scattering interferometry, the apparatus comprising
      i. a substrate;
      ii. a channel formed in the substrate capable of receiving the liquid sample to be analyzed;
      iii. a light source for generating a light beam;
      iv. a photodetector for receiving scattered light and generating intensity signals; and
      v. at least one signal analyzer capable of receiving the intensity signals and determining therefrom one or more characteristic properties of the liquid sample; and
   b. interrogating the liquid sample using backscattering interferometry, wherein the liquid sample comprises at least two binding partners in a solvent selected from ketone, aldehyde, alkane, chlorocarbon, sulfoxide, and acetonitrile, and wherein a molecular interaction between the binding partners is detected in the liquid sample via the interrogation.

2. The method of claim 1, further comprising measuring an end-point value for the reaction between the binding partners.

3. The method of claim 1, wherein further comprising determining kinetic parameters of the molecular interaction.

4. The method of claim 1, wherein the solvent is acetonitrile.

5. The method of claim 1, wherein the molecular interaction comprises hydrogen bonding.

6. The method of claim 1, wherein interrogating is performed in at least two discrete locations along a length of the channel substantially simultaneously.

7. The method of claim 1, wherein the molecular interaction is an antibody-antigen interaction.

8. The method of claim 1, wherein both of the two binding partners are free-solution species.

9. A method for determining a molecular interaction comprising the steps of:
   a. providing a substrate having a channel formed therein for reception of a liquid sample to be analyzed;
   b. introducing the liquid sample to be analyzed into the channel, wherein the liquid sample comprises at least two binding partners in a solvent selected from hydrocarbon and acetonitrile;
   c. directing a light beam from a light source onto the substrate such that the light beam is incident on at least a portion of the liquid sample to generate scattered light through reflective and refractive interaction of the light beam with a substrate/channel interface, and the liquid sample, wherein the scattered light comprising interference fringe patterns including a plurality of spaced light bands whose positions shift in response to changes in the refractive index of the sample;
   d. detecting positional shifts in the light bands; and
   e. determining the molecular interaction between the binding partners in the liquid sample from the positional shifts of the light bands in the interference fringe patterns.

10. The method of claim 9, wherein detecting is performed with a photodetector array.

11. The method of claim 9, wherein the molecular interaction comprises hydrogen bonding.

12. The method of claim 9, wherein the molecular interaction is an antibody-antigen interaction.

13. The method of claim 9, wherein the substrate and channel together comprise a capillary tube.

14. The method of claim 9, wherein the substrate and channel together comprise a microfluidic device.

15. The method of claim 14, wherein the microfluidic device comprises a silica substrate and an etched channel formed in the substrate for reception of a sample, the channel having a cross sectional shape.

16. The method of claim 9, wherein the solvent is acetonitrile.

17. A method comprising the steps of:
   a. interrogating a liquid sample comprising at least two binding partners in a solvent selected from hydrocarbon, ketone, aldehyde, alkane, chlorocarbon, sulfoxide, and acetonitrile by using backscattering interferometry, and
   b. detecting a change in refractive index of the liquid sample due to a molecular interaction between the binding partners.

18. The method of claim 17, wherein the solvent comprises acetonitrile.

19. The method of claim 17, wherein the molecular interaction comprises hydrogen bonding.

20. The method of claim 17, wherein both of the binding partners are free-solution species.

* * * * *

UNITED STATES PATENT AND TRADEMARK OFFICE
CERTIFICATE OF CORRECTION

PATENT NO. : 9,562,853 B2
APPLICATION NO. : 13/402104
DATED : February 7, 2017
INVENTOR(S) : Darryl J. Bornhop, Robert A. Flowers and Esther Pesciotta Miller Page 1 of 1

It is certified that error appears in the above-identified patent and that said Letters Patent is hereby corrected as shown below:

On the Title Page

Replace "(73) Assignee: Vanderbilt University, Nashville, TN (US)"
with --(73) Assignee: Vanderbilt University, Nashville, TN (US)
Lehigh University, Bethlehem, PA (US)--

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*